(12) United States Patent
Miyake et al.

(10) Patent No.: US 10,610,821 B2
(45) Date of Patent: Apr. 7, 2020

(54) DEODORIZING APPARATUS AND DEODORIZING METHOD

(71) Applicant: Panasonic Intellectual Property Management Co., Ltd., Osaka (JP)

(72) Inventors: Gaku Miyake, Osaka (JP); Genichiro Matsuda, Nara (JP); Takahiro Kitai, Hyogo (JP); Yoshio Yamada, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 73 days.

(21) Appl. No.: 15/956,373

(22) Filed: Apr. 18, 2018

(65) Prior Publication Data

US 2018/0345210 A1  Dec. 6, 2018

(30) Foreign Application Priority Data

May 30, 2017  (JP) .................................. 2017-106978

(51) Int. Cl.
*B01D 53/18*  (2006.01)
*H05H 1/24*  (2006.01)
(Continued)

(52) U.S. Cl.
CPC .............. *B01D 53/18* (2013.01); *A61L 9/145* (2013.01); *A61L 9/22* (2013.01); *B01D 3/346* (2013.01);
(Continued)

(58) Field of Classification Search
CPC ........ A61L 9/145; A61L 9/22; A61L 2209/11; A61L 2209/213; A61L 2209/22; B01D 3/346; B01D 17/0205; B01D 17/12; B01D 53/00; B01D 53/18; B01D 53/326; B01D 53/965; B01D 2251/106; B01D 2252/103; B01D 2257/102; B01D 2257/204; B01D 2257/708; B01D 2257/90; B01D 2257/91; B01D 2258/06; B01D 2259/4508; B01D 2259/818; H05H 1/24; H05H 1/2406; H05H 2245/121
See application file for complete search history.

(56) References Cited

U.S. PATENT DOCUMENTS

2013/0334955 A1  12/2013  Salton et al.
2016/0120013 A1  4/2016  Imai
(Continued)

FOREIGN PATENT DOCUMENTS

JP  2005-074311  3/2005
JP  4041224 B  1/2008
(Continued)

*Primary Examiner* — Timothy C Cleveland
(74) *Attorney, Agent, or Firm* — Wenderoth, Lind & Ponack, L.L.P.

(57) ABSTRACT

Plasma is generated in a gas phase in a processing tub to produce a reforming component, the produced reforming component is dissolved in a liquid and is dispersed in the liquid to produce a reforming liquid, the produced reforming liquid is discharged from the processing tub to be stored in the storage tub, and gas is supplied from a gas supplier into the reforming liquid in the storage tub. The supplied gas has a bubble shape, comes into contact with the reforming liquid stored in the storage tub, and is deodorized.

15 Claims, 23 Drawing Sheets

(51) Int. Cl.
  *B01D 53/32* (2006.01)
  *B01D 17/12* (2006.01)
  *B01D 3/34* (2006.01)
  *B01D 17/02* (2006.01)
  *A61L 9/22* (2006.01)
  *B01D 53/96* (2006.01)
  *A61L 9/14* (2006.01)

(52) U.S. Cl.
  CPC ......... *B01D 17/0205* (2013.01); *B01D 17/12* (2013.01); *B01D 53/326* (2013.01); *B01D 53/965* (2013.01); *H05H 1/24* (2013.01); *H05H 1/2406* (2013.01); *A61L 2209/11* (2013.01); *A61L 2209/213* (2013.01); *A61L 2209/22* (2013.01); *B01D 2251/106* (2013.01); *B01D 2252/103* (2013.01); *B01D 2257/102* (2013.01); *B01D 2257/204* (2013.01); *B01D 2257/708* (2013.01); *B01D 2257/90* (2013.01); *B01D 2257/91* (2013.01); *B01D 2258/06* (2013.01); *B01D 2259/4508* (2013.01); *B01D 2259/818* (2013.01); *H05H 2001/2412* (2013.01); *H05H 2245/121* (2013.01)

(56) References Cited

U.S. PATENT DOCUMENTS

2016/0228844 A1* 8/2016 Mededovic ........... C02F 1/4608
2017/0021049 A1  1/2017 Ohyama et al.

FOREIGN PATENT DOCUMENTS

| JP | 2012-204249 | 10/2012 |
| JP | 2016-083658 | 5/2016 |
| JP | 2017-023726 | 2/2017 |

* cited by examiner

DEODORIZING APPARATUS AND DEODORIZING METHOD

TECHNICAL FIELD

The technical field relates to a deodorizing apparatus and a deodorizing method for decomposing an odorous substance in gas by causing a reforming liquid which is produced by electrochemically processing a liquid to come into contact with the gas. More particularly, the technical field relates to a deodorizing apparatus and a deodorizing method in which a reforming liquid having a sterilizing operation and a deodorizing operation is produced by reforming a liquid by generating plasma in the liquid, and an odorous component in gas is decomposed in the produced reforming liquid.

BACKGROUND

FIG. 15 illustrates an example of a reforming liquid producing device of the related art. A reforming liquid producing device, in which first electrode 801 and second electrode 802 are disposed in liquid 803 (for example, water), a high voltage pulse is applied between both electrodes 801 and 802 from pulse power supply 804 to evaporate liquid 803 and generate plasma 805, thereby producing a reforming liquid containing a component having, for example, oxidizing power such as a hydroxyl radical (OH radical) or hydrogen peroxide, is known. Particularly, it is known that the OH radical has high oxidizing power and a high sterilizing operation and is provided by mixing the reforming liquid containing these components. The OH radical has a high sterilizing operation with respect to, for example, bacteria. In addition, it is known that when plasma 805 is covered by liquid 803 a liquid-derived component is easily generated by generating plasma 805 in liquid 803. For example, it is known that the OH radical or hydrogen peroxide is easily produced by generating plasma 805 in water.

However, in a case of the reforming liquid producing device of the related art, not only is a high applying voltage required for evaporating liquid 803 but also the generation efficiency of plasma 805 is low. There is also a problem that it takes a long period of time to reform liquid 803.

Therefore, a reforming liquid producing device, in which gas introduced from an outside is interposed between both electrodes to improve the generation efficiency of plasma while lowering the applying voltage, is known (see Japanese Patent No. 4041224). In the reforming liquid producing device (FIG. 16) disclosed in Japanese Patent No. 4041224, gas 904 (for example, oxygen) is interposed between anode electrode 901 and cathode electrode 902 together with processed liquid 903, and a pulse voltage is applied between both electrodes 901 and 902. Plasma is generated in gas 904 and reformation of processed liquid 903 is generated on a contact surface between the plasma and the processed liquid 903 by applying the pulse voltage. According to the reforming liquid producing device disclosed in Japanese Patent No. 4041224, it is possible to reduce the applying voltage and to perform reformation of processed liquid 903 by efficiently generating plasma as compared to a case where gas is not interposed.

SUMMARY

Here, a deodorizing apparatus that decomposes the odorous component in the gas by causing the reforming liquid to come into contact with the gas is considered.

However, in a case where the reforming liquid producing device disclosed in Japanese Patent No. 4041224 is applied to the deodorizing apparatus, there is a problem that a generation efficiency of plasma is low and it takes a long period of time for a deodorizing process of the gas.

The disclosure is made in view of the situation and an object of the disclosure is to provide a deodorizing apparatus and a deodorizing method in which a liquid can be rapidly reformed, and the deodorizing process of gas can be performed in a short period of time by efficiently generating plasma.

According to an aspect of the disclosure, there is provided a deodorizing apparatus including: a processing tub that generates a gas phase in the vicinity of a swirling center of a swirling flow of a liquid by swirling the liquid introduced from an introduction portion around a center axis and includes a discharge portion that discharges the liquid as a reforming liquid after swirling the liquid introduced from the introduction portion between the introduction portion and the discharge portion and generating the swirling flow; a first electrode of which at least apart is disposed in the processing tub and comes into contact with the liquid in the processing tub; a second electrode that is disposed so as to come into contact with the liquid in the processing tub; a power supply that generates plasma in the gas phase by applying a voltage between the first electrode and the second electrode to produce a reforming component in the reforming liquid; a storage tub that includes a reforming liquid supplier to which the discharge portion of the processing tub is connected and the reforming liquid is supplied, and a gas discharge portion which discharges gas after deodorization to an upper portion above the reforming liquid supplier, and generates the plasma in the gas phase in the processing tub to produce the reforming component, and in which the produced reforming component is dissolved in the liquid and is dispersed in the liquid to produce the reforming liquid, and the produced reforming liquid is discharged from the processing tub and is stored; and a gas supplier that supplies gas into the reforming liquid in the storage tub. The gas is supplied from the gas supplier into the storage tub, and the supplied gas has a bubble shape and comes into contact with the reforming liquid stored in the storage tub to be deodorized.

According to another aspect of the disclosure, there is provided a deodorizing method including: a step of generating a gas phase in the vicinity of a swirling center of a swirling flow of a liquid in a processing tub by swirling the liquid introduced into the processing tub; a step of producing a reforming liquid by applying a voltage to the generated gas phase, generating plasma in the gas phase to produce a reforming component, dissolving the produced reforming component in the liquid, and dispersing the produced reforming component in the liquid; and a deodorizing step of supplying gas from a gas supplier into a storage tub in a state where the produced reforming liquid is stored in the storage tub, and causing the supplied gas to be a bubble shape, to come into contact with the reforming liquid stored in the storage tub, and to be deodorized.

According to the deodorizing apparatus and the deodorizing method of the aspects of the disclosure, the liquid can be evaporated in the swirling flow and the reforming liquid having the reforming component can be produced by generating plasma by applying the pulse voltage to the produced gas phase. Since it is unnecessary to evaporate the liquid by applying the voltage, plasma can be generated and reformation of the liquid can be performed efficiently and rapidly with less electric power. As a result, the deodorizing process of the gas can be performed in a short period of time.

DESCRIPTION OF EMBODIMENTS

Embodiment 1

Figure 1:
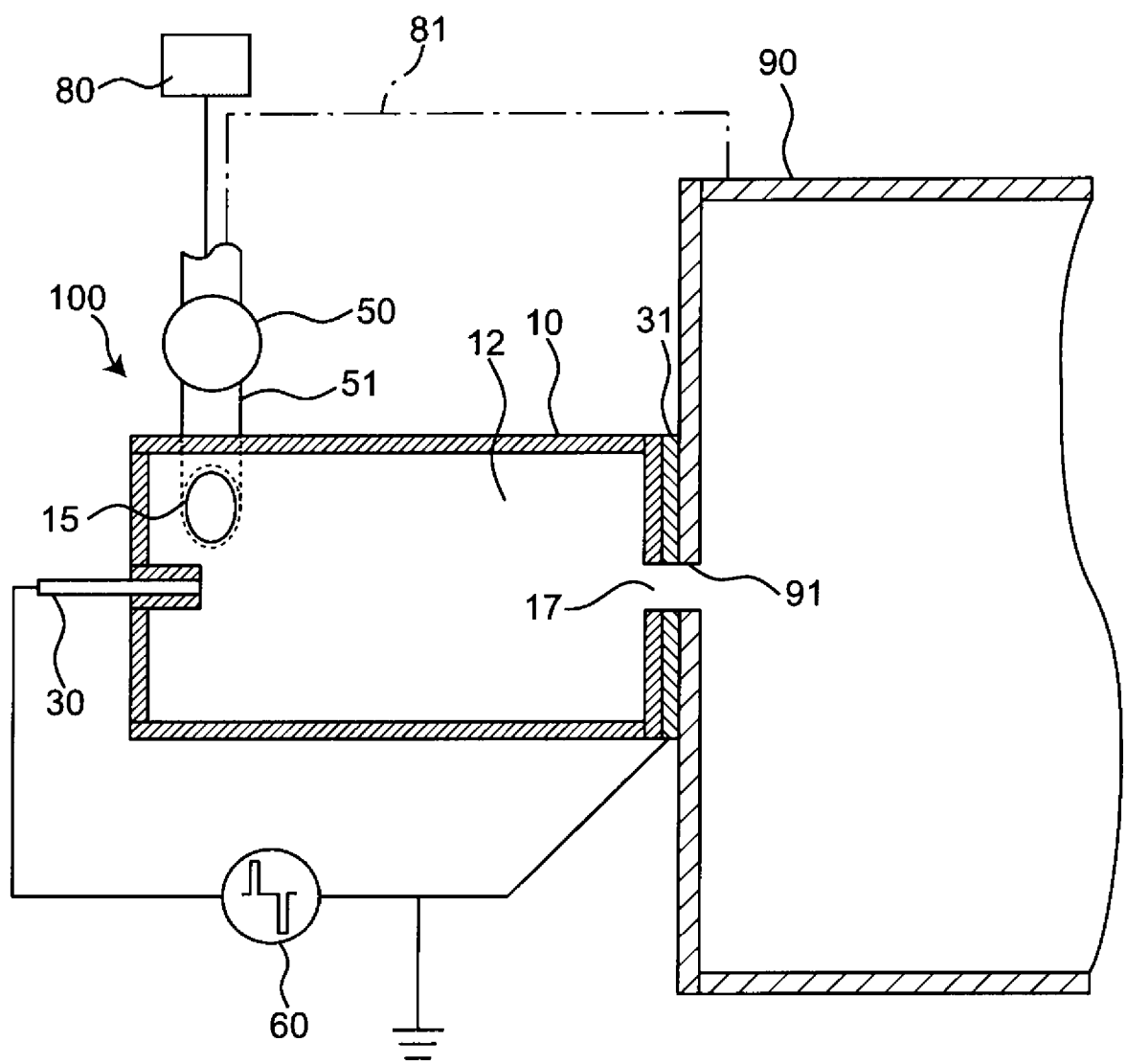
FIG. 1 is a side sectional view illustrating a configuration of a reforming liquid producing device of a deodorizing apparatus of Embodiment 1 of the disclosure.
Figure 1:
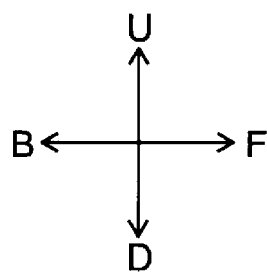

Hereinafter, deodorizing apparatus 101 including reforming liquid producing device 100 according to the embodiment of the disclosure will be described in detail with reference to the drawings. The same reference numerals are given to the same portion or corresponding portions in the drawings and description thereof will not be repeated. In order to make the explanation easy to understand, in the drawings referred to below, a configuration is simplified or schematically illustrated, and some constituent members are omitted. In addition, a dimensional ratio between the constituent members shown in each drawing does not necessarily indicate the actual size ratio.

Entire Configuration

Figure 6A:
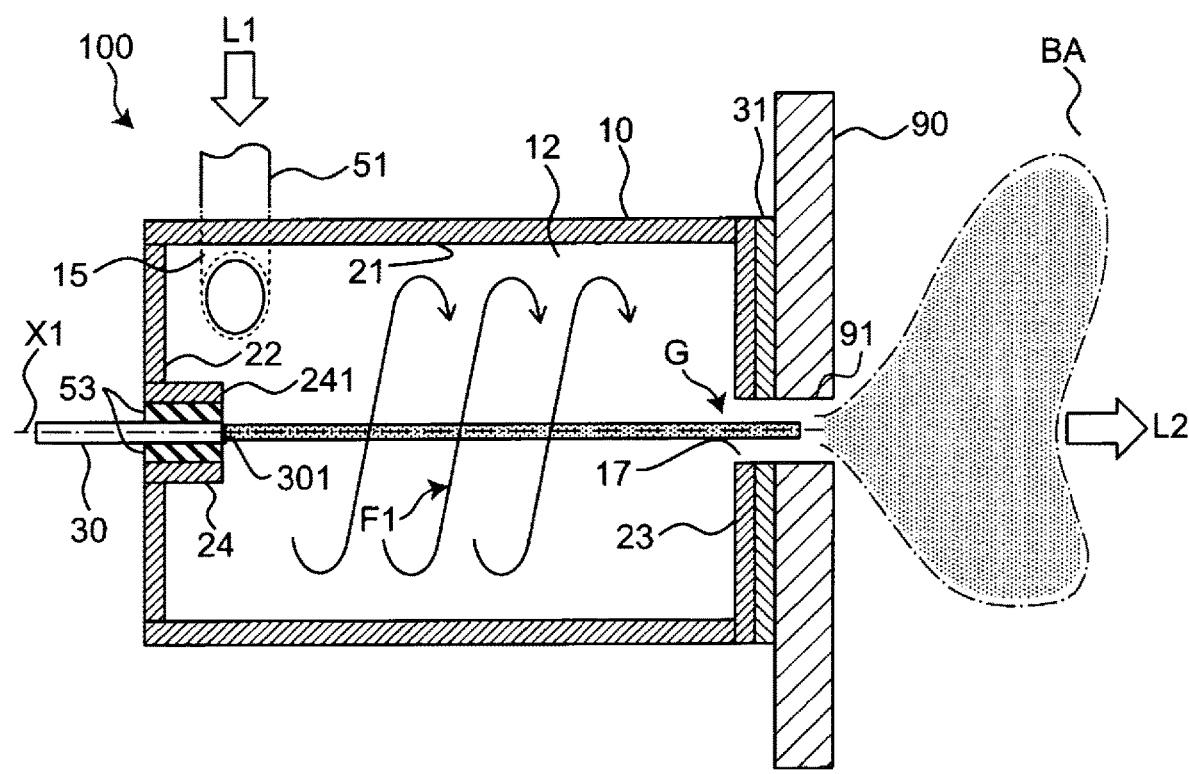
FIG. 6A is a side sectional view illustrating a state where the swirling flow is generated on the inside of the processing tub and a voltage is applied.
Figure 6A:
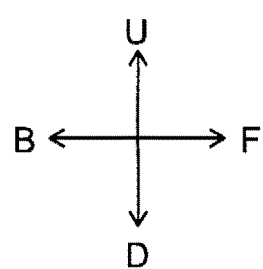
Figure 6B:
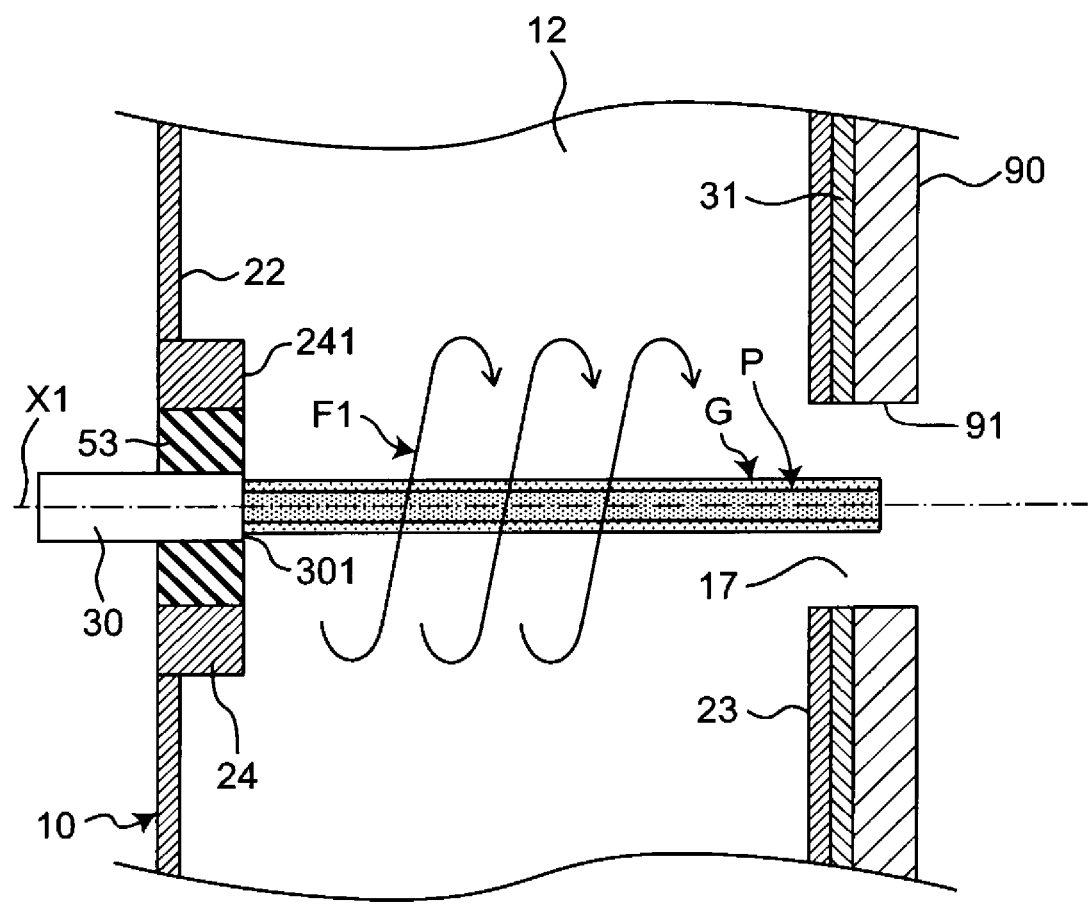
FIG. 6B is a partial enlarged view of a state where plasma is generated in a gas phase of FIG. 6A.
Figure 6B:
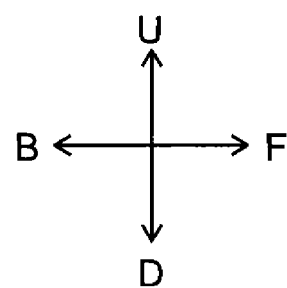
Figure 6C:
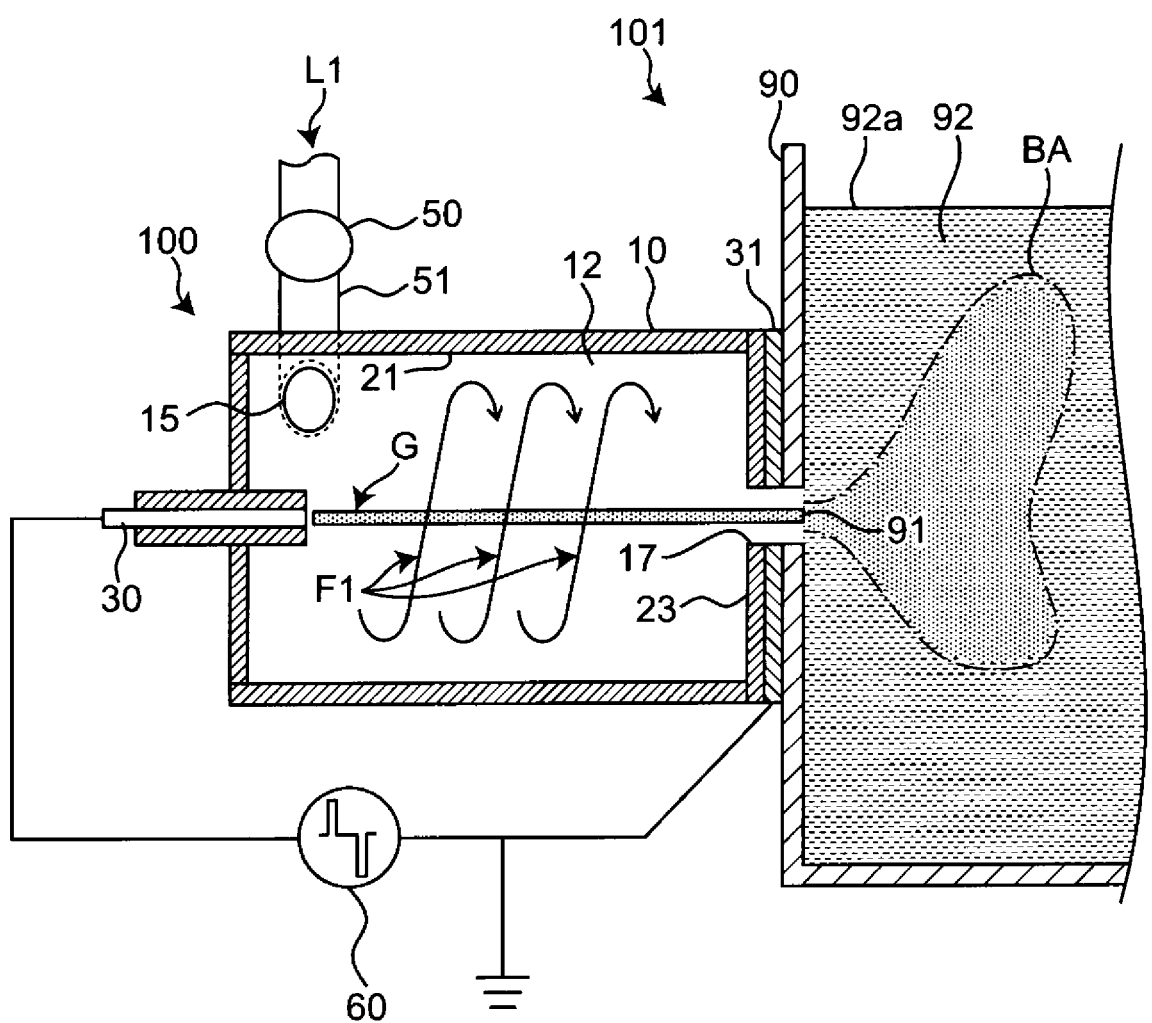
FIG. 6C is a side sectional view of a state where a reforming liquid is supplied to a storage tub of the deodorizing apparatus.
Figure 6D:
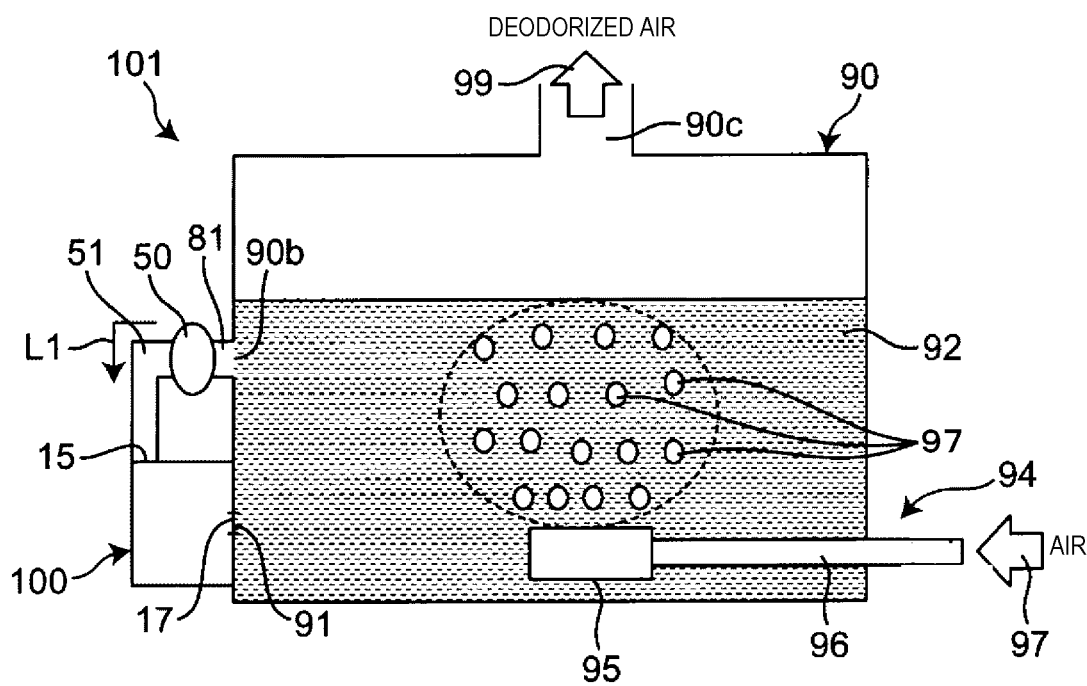
FIG. 6D is a side sectional view of an entire deodorizing apparatus in a state where gas is supplied to the storage tub of the deodorizing apparatus and a deodorizing process is performed.

Deodorizing apparatus 101 includes at least reforming liquid producing device 100 and gas supplier 94 (see FIG. 6D). Reforming liquid producing device 100 functions as a device that produces reforming liquid L2 used for a deodorizing process.

First, an entire configuration of reforming liquid producing device 100 according to Embodiment 1 will be described. FIG. 1 is a side sectional view illustrating a configuration of reforming liquid producing device 100 according to Embodiment 1 of the disclosure. In the following drawings, arrow F indicates a forward direction and arrow B indicates a backward direction of reforming liquid producing device 100. Arrow U indicates an upward direction and arrow D indicates a downward direction. Arrow R indicates a rightward direction as viewed from the backward direction and arrow L indicates a leftward direction as viewed from the backward direction.

Reforming liquid producing device 100 produces a reforming component by discharging in a liquid and produces reforming liquid L2 by dispersing the produced reforming component in the liquid. In Embodiment 1, a case where circulation water L1 as an example of a liquid is reformed and reforming liquid L2 containing a reforming component such as an OH radical or hydrogen peroxide is produced will be described. Here, circulation water L1 means a liquid that is storage water 92 held and stored in storage tub 90, which is supplied to processing tub 12 by a pump that is an example of liquid supplier 50 through circulation pipe 81 and pipe 51. Storage water 92 also includes reforming liquid L2 of a state of water or hot water supplied from reforming liquid producing device 100 to storage tub 90. The reforming liquid of which a deodorizing operation is performed by deodorizing a gas 97 such as air in reforming liquid L2. As another example of circulation water L1, a valve is disposed instead of a pump so that tap water or the like can be supplied to processing tub 12 by opening and closing the valve.

Reforming liquid producing device 100 includes at least a processing tub 12, first electrode 30, second electrode 31, and power supply 60. More specifically, the reforming liquid producing device 100 includes a device body 10, liquid supplier 50, storage tub 90, and power supply 60. The device body 10 includes a processing tub 12, introduction portion 15, discharge portion 17, first electrode 30, and second electrode 31.

Processing tub 12 is a portion that produces reforming liquid L2 by producing a reforming component by plasma in circulation water L1 introduced inside. A material of processing tub 12 may be an insulator or a conductor. In a case of a conductor, it is necessary to interpose an insulator between electrodes 30 and 31. When the reforming component is discharged to storage tub 90, the reforming component is dispersed in circulation water L1 and reforming liquid L2 is produced.

Processing tub 12 includes a columnar processing chamber having a circular front sectional shape. Introduction portion 15 is disposed at one end of processing tub 12 to introduce circulation water L1 into processing tub 12 from a tangential direction of a circular sectional shape orthogonal to center axis X1 of processing tub 12. Introduction portion 15 communicates with liquid supplier 50 via pipe 51. Discharge portion 17 is disposed at the other end of processing tub 12 to discharge circulation water L1 introduced into processing tub 12 and the reforming component produced in processing tub 12 from processing tub 12 to storage tub 90. In Embodiment 1, discharge portion 17 is connected to reforming liquid supplier 91 of storage tub 90.

First electrode 30 is disposed inside at one end of processing tub 12. First electrode 30 protrudes from a center of an inner wall at one end of processing tub 12 into processing tub 12 along a longitudinal direction.

Second electrode 31 is disposed outside the wall at the other end of processing tub 12 to be disposed in the vicinity of discharge portion 17.

First electrode 30 is connected to power supply 60 and second electrode 31 is grounded. A pulse voltage of a high voltage is applied to first electrode 30 and second electrode 31 by power supply 60. As a material of first electrode 30, for example, tungsten is used.

Liquid supplier 50 is, for example, a pump that supplies circulation water L1 into processing tub 12. Liquid supplier 50 is connected to pipe 51. One end of pipe 51 is connected to introduction portion 15 as an inside opening disposed in the vicinity of the inner wall of one end of processing tub 12 and the other end of pipe 51 is connected to the liquid supply source (not illustrated) (for example, water tank 80) or in a form in which storage water containing the reforming liquid of storage tub 90 can be circulated.

Power supply 60 applies the pulse voltage of a high voltage between first electrode 30 and second electrode 31. Power supply 60 can apply a so-called bipolar pulse voltage that alternately applies a positive pulse voltage and a negative pulse voltage.

Storage tub 90 is a tub for shearing the reforming component discharged from reforming liquid producing device 100, producing micro-bubbles or nano-bubbles containing the reforming component, and diffusing the micro-bubbles or nano-bubbles in water. Specifically, storage tub 90 includes therein a cross-sectional area larger than a cross-sectional area of the opening of discharge portion 17 of processing tub 12, shears the reforming component discharged from discharge portion 17 into storage tub 90, produces micro-bubbles or the micro-bubbles and nano-bubbles containing the reforming component in storage tub 90, and diffuses produces micro-bubbles or the micro-bubbles and nano-bubbles in water. Therefore, storage tub 90 functions as a micro-bubble producing tub. The reforming liquid L2 containing micro-bubbles or nano-bubbles and reliably performing sterilization can be produced in storage tub 90 by securing an inner diameter or one side that is greater than or equal to twice an inner diameter dimension of the opening of discharge portion 17 of processing tub 12.

As illustrated in FIG. 6D, storage tub 90 includes reforming liquid supplier 91, gas discharge portion 90c, and a storage water discharge portion 90b. The liquid supplier 91 is disposed at a lower portion or an intermediate portion and is connected to discharge portion 17 of processing tub 12.

The gas discharge portion 90c is disposed at, for example, a center of an upper portion above reforming liquid supplier 91. The storage water discharge portion 90b is disposed at an intermediate portion between reforming liquid supplier 91 and gas discharge portion 90c. Plasma P is generated in gas phase G in processing tub 12 to produce the reforming component. The produced reforming component is dissolved in a liquid and is dispersed in the liquid to produce reforming liquid L2. The produced reforming liquid L2 is discharged from discharge portion 17 of processing tub 12 to reforming liquid supplier 91 of storage tub 90 to be stored in storage tub 90.

In FIG. 6D, pipe 51 is connected to storage water discharge portion 90b of storage tub 90 to configure circulation pipe 81. Storage water 92 in storage tub 90 is supplied as circulation water L1 from introduction portion 15 into processing tub 12 via circulation pipe 81 and liquid supplier 50. Reforming liquid L2 discharged from processing tub 12 via discharge portion 17 is introduced from reforming liquid supplier 91 into storage tub 90. Therefore, the liquid circulates between reforming liquid producing device 100 and storage tub 90. Also, in Embodiments 2 and 3, the same configuration is provided.

In addition to reforming liquid producing device 100, deodorizing apparatus 101 further includes gas supplier 94.

Gas supplier 94 can supply gas 97 to be processed in a bubble shape into storage tub 90. Therefore, supplied bubble-shaped gas 97 to be processed comes into contact with reforming liquid L2 so that deodorization may be performed. Therefore, gas 97 to be processed may be directly supplied to storage tub 90 in a bubble shape or may be indirectly supplied from a reforming liquid producing device side to storage tub 90. An example in which gas 97 to be processed is directly supplied to storage tub 90 will be described here. Indirect supply from the reforming liquid producing device side will be described in Embodiments 2 and 3.

Storage tub 90 includes gas discharge portion 90c of storage tub 90 and gas blowout unit 95 that is disposed below reforming liquid supplier 91 and blows out gas 97 into reforming liquid L2 in storage tub 90. Gas blowout unit 95 is configured of gas supply pipe 96, a porous member having a large number of through-holes, and the like. If necessary, a pump may be disposed as a gas supply device. Gas 97 to be processed such as air supplied from outside of storage tub 90 is bubbled from gas blowout unit 95 via gas supply pipe 96 and is blown out into storage water 92 in a bubble shape. As described above, gas 97 to be processed is bubbled so that an odorous component of gas 97 is decomposed as the reforming component of reforming liquid L2, thereby being deodorized. Deodorized gas 99 advances upward in storage water 92 that is reforming liquid L2 and is discharged from gas discharge portion 90c disposed at an upper portion of storage tub 90 to the outside of storage tub 90.

Device Body

Figure 2:
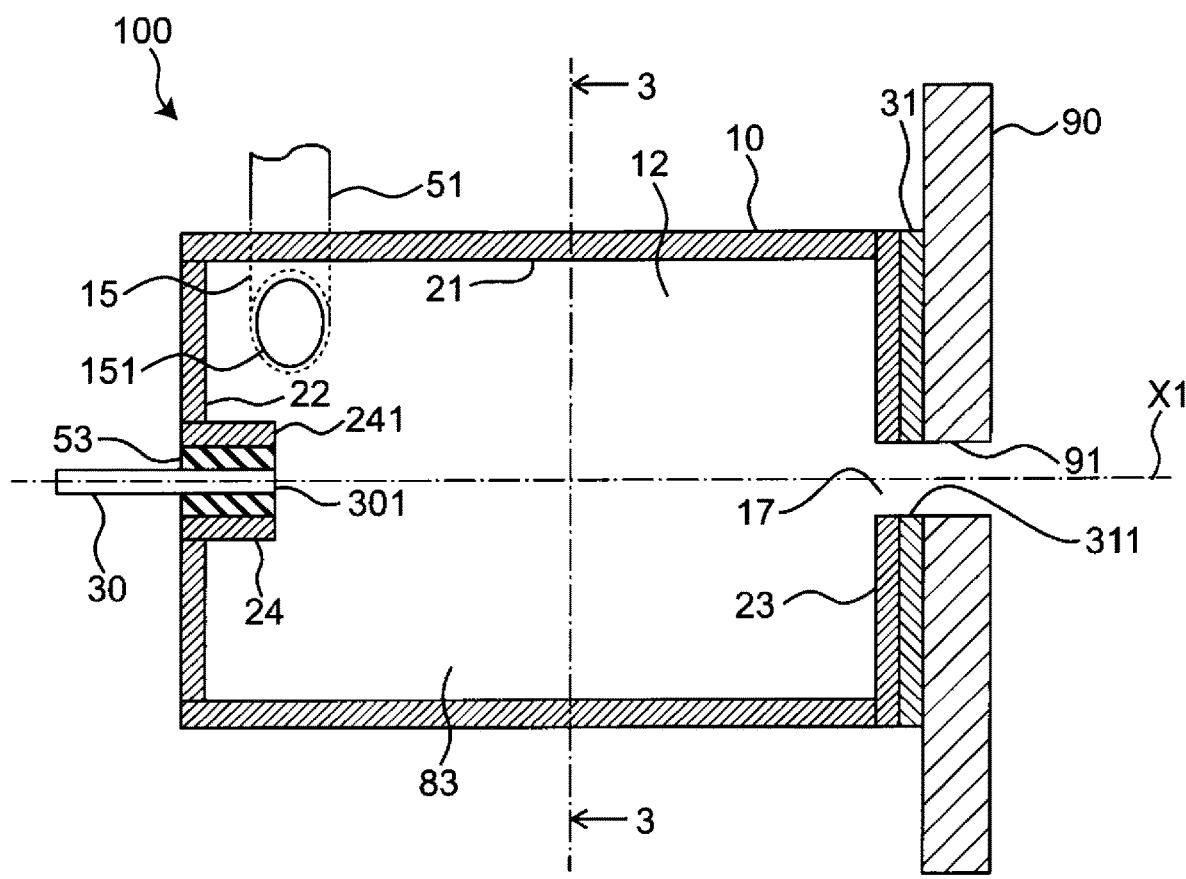
FIG. 2 is a side sectional view of a device body.
Figure 2:
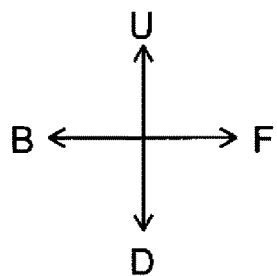

Next, device body 10 will be described in detail. FIG. 2 is a side sectional view of device body 10.

Processing tub 12 includes first inner wall 21, second inner wall 22, and third inner wall 23. First inner wall 21 is a cylindrical wall portion. Second inner wall 22 is provided at a left end portion of first inner wall 21 in FIG. 2. Third inner wall 23 is provided at a right end portion of first inner wall 21 in FIG. 2. Second inner wall 22 and third inner wall 23 have substantially a circular shape in a side view. Substantially columnar accommodating space 83 is configured inside processing tub 12 by first inner wall 21, second inner wall 22, and third inner wall 23. A center axis of first inner wall 21, that is, a virtual center axis of substantially columnar accommodating space 83 configuring the inside of processing tub 12 is referred to as center axis X1.

In second inner wall 22, cylindrical electrode support tube 24 protruding into accommodating space 83 is provided at a center. Electrode support tube 24 is cylindrical and extends in the rightward direction. Electrode support tube 24 is disposed so that a center axis thereof matches center axis X1. First electrode 30 is supported on the inside of electrode support tube 24 via insulator 53. First electrode 30 has a rod shape and insulator 53 is disposed around first electrode 30. First electrode 30 is disposed so that an axis thereof in the longitudinal direction matches center axis X1. An inside end surface of right end portion 301 of first electrode 30, an inside end surface of insulator 53, and inside end surface 241 of electrode support tube 24 are configured so as to be disposed substantially in the same plane.

Figure 3:
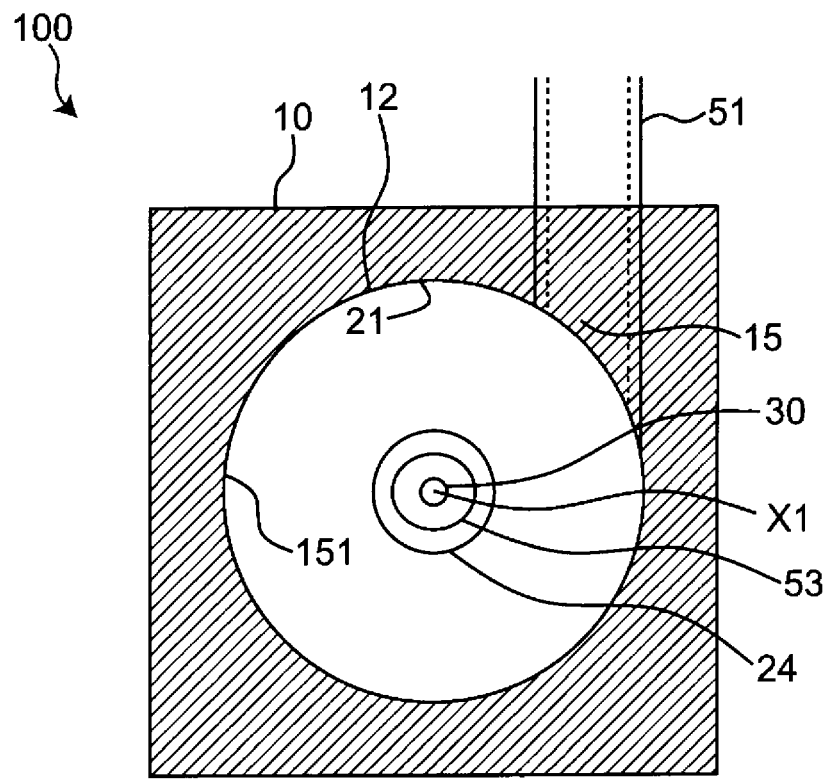
FIG. 3 is a sectional view which is taken along line 3-3 of FIG. 2.
Figure 3:
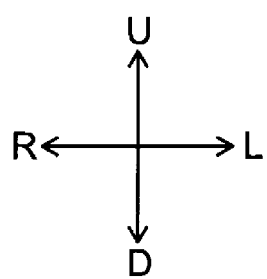

Introduction portion 15 penetrates device body 10 and one opening end 151 is formed on first inner wall 21. Introduction portion 15 is disposed at a position adjacent to second inner wall 22 in a side view. In addition, FIG. 3 is a sectional view which is taken along line 3-3 of FIG. 2. Introduction portion 15 is disposed on the wall surface of first inner wall 21.

Discharge portion 17 penetrates a center portion of third inner wall 23. Discharge portion 17 is formed so that a center axis thereof matches center axis X1.

Second electrode 31 is a plate-like metal member and opening 311 is formed at the center portion. Opening 311 has a circular shape and is formed so that a center axis thereof matches center axis X1.

Operation

Figure 4:
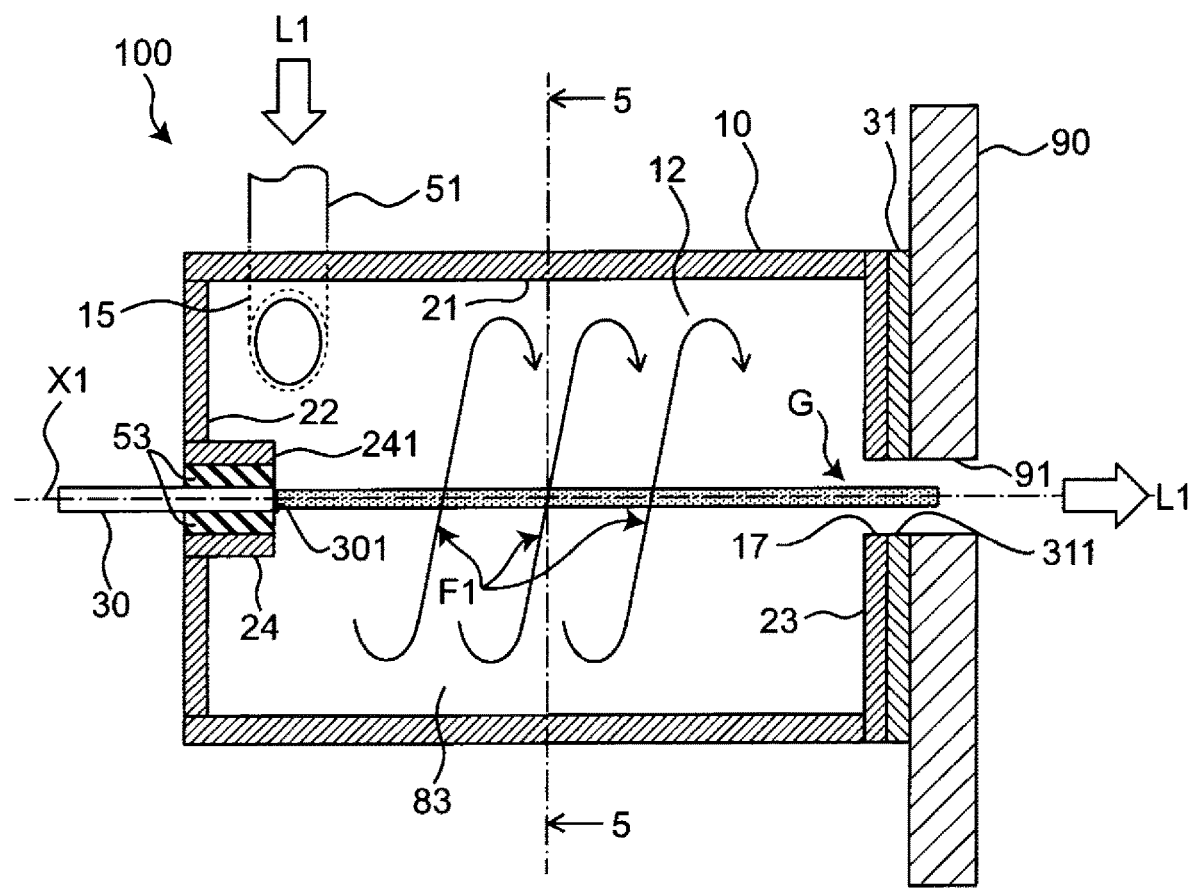
FIG. 4 is a side sectional view illustrating a state where a swirling flow is generated on an inside of a processing tub and a voltage is not applied.
Figure 4:
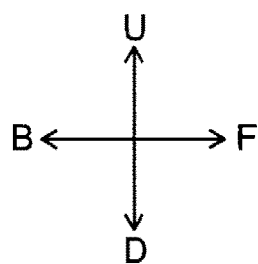

Next, first, as a reforming liquid producing process, a reforming liquid producing operation of reforming liquid producing device 100 will be described. Hereinafter, for the sake of convenience of description, a state where gas phase G is generated inside processing tub 12 (FIGS. 4 and 5) and a state where plasma P is generated by applying a pulse voltage to generated gas phase G (FIGS. 6A and 6B) are described separately. FIG. 4 is a side sectional view illustrating a state where swirling flow F1 is generated on the inside of processing tub 12 and the pulse voltage is not applied.

First, as illustrated in FIG. 4, when storage water 92 of storage tub 90 is sucked by the pump and circulation water L1 is introduced from introduction portion 15 into processing tub 12 at a predetermined pressure, circulation water L1 moves from introduction portion 15 to the right side of FIG. 4 while generating swirling flow F1 along first inner wall 21. Swirling flow F1 moving to the right side of FIG. 4 while swirling moves toward discharge portion 17.

A pressure in the vicinity of center axis X1 is lowered to less than or equal to a saturated water vapor pressure and a part of circulation water L1 is evaporated to generate vaporized water by swirling flow F1. Therefore, gas phase G is produced in the vicinity of center axis X1. Gas phase G is generated in the vicinity of a swirling center, specifically, from right end portion 301 of first electrode 30 to the vicinity of opening 311 of second electrode 31 along center axis X1. In addition, gas phase G is swirled in the same direction as that of swirling flow F1 by coming into contact with swirling flow F1. Swirling gas phase G is sheared by the microbubbles or nano-bubbles because of resistance of storage water 92 in storage tub 90 in the vicinity of discharge portion 17, and is diffused into storage water 92 of storage tub 90.

Figure 5:
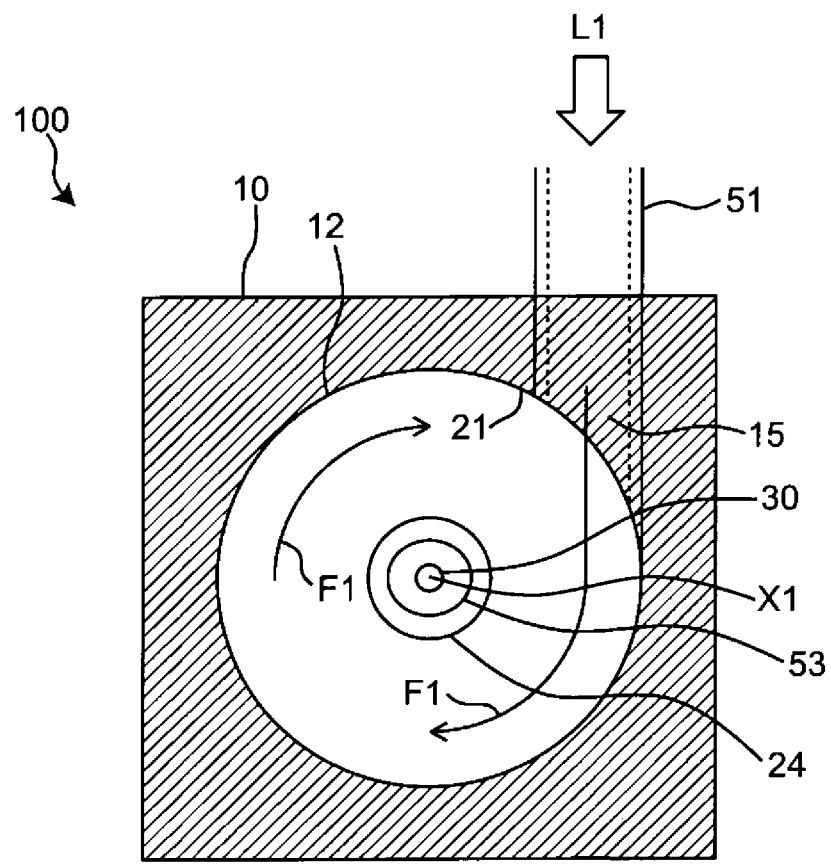
FIG. 5 is a sectional view which is taken along line 5-5 of FIG. 4.
Figure 5:
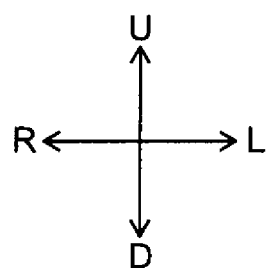

FIG. 5 is a sectional view which is taken along line 5-5 of FIG. 4. As described in FIG. 4, when circulation water L1 is introduced from introduction portion 15 into processing tub 12 at a predetermined pressure, circulation water L1 generates swirling flow F1 clockwise in FIG. 5 along first inner wall 21. Circulation water L1 is swirled on the inside of processing tub 12 and thereby there is a pressure in the vicinity of the center of swirling flow F1. That is, in the vicinity of center axis X1, pressure is lowered to less than or equal to the saturated water vapor pressure and water vapor which is obtained by evaporating a part of circulation water L1 is generated in the vicinity of center axis X1, thereby producing gas phase G.

FIGS. 6A and 6B are side sectional views illustrating a state where swirling flow F1 is generated on the inside of processing tub 12 and the pulse voltage is applied. As illustrated in FIG. 6A, in a state where gas phase G evaporated from circulation water L1 is generated from the vicinity of first electrode 30 to the vicinity of second electrode 31, the pulse voltage of a high voltage is applied between first electrode 30 and second electrode 31 by power supply 60. FIG. 6B is an enlarged view of a state where plasma P is generated in gas phase G. When the pulse voltage of a high voltage is applied between first electrode 30 and second electrode 31, plasma P is generated in gas phase G and a radical (OH radical or the like), a compound (hydrogen peroxide or the like), or ions which is water-derived as the reforming component is produced. Gas phase G containing the reforming component is swirled in the same direction as that of swirling flow F1 by swirling flow F1 in a periphery. Gas phase G containing the reforming component is swirled and thereby a part of the reforming component is dissolved to a swirling flow F1 side. Therefore, the reforming component in circulation water L1 is dispersed to produce reforming liquid L2. In addition, gas phase G containing the reforming component in the vicinity of discharge portion 17 is sheared by receiving the resistance of reforming liquid L2 in storage tub 90 and bubble BA containing the reforming component is generated. In addition, air is prevented from mixing into gas phase G which is in a negative pressure by storing reforming liquid L2 above discharge portion 17 in storage tub 90. As described above, in a state where the reforming component produced by plasma P is bubbled or is dissolved and dispersed in reforming liquid L2, reforming liquid L2 is stored in storage tub 90 to change all storage water 92 in storage tub 90 to reforming liquid L2.

Next, a deodorizing process is started. That is, gas 97 to be processed is supplied from gas supplier 94 into storage water 92 of storage tub 90 to perform the deodorizing process of gas 97. Specifically, it is as follows.

Gas 97 to be processed such as air is bubbled from gas blowout unit 95 via gas supply pipe 96 and is blown out in a babble shape in storage water 92 from the outside of storage tub 90. Gas 97 to be processed is bubbled so that the odorous component of gas 97 comes into contact with the reforming component of reforming liquid L2 to be decomposed, and thereby the deodorizing process is performed.

Deodorized gas 99 advances upward in storage water 92 that is reforming liquid L2 and is discharged from gas discharge portion 90c disposed at the upper portion of storage tub 90 to the outside of storage tub 90. When gas 97 is supplied from gas supplier 94 into storage water 92 of storage tub 90, generation of plasma P is stopped to prevent generation of nitrous acid in reforming liquid producing device 100.

When the deodorizing process is completed, gas supply is stopped, reforming liquid L2 is generated in reforming liquid producing device 100, and a reforming liquid producing process is performed so that all storage water 92 of storage tub 90 becomes reforming liquid L2. When the reforming liquid producing process is completed, the deodorizing process described above is performed again.

According to Embodiment 1 described above, circulation water L1 is evaporated in swirling flow F1 and a pulse voltage is applied to generated gas phase G to generate plasma P, thereby producing reforming liquid L2 containing the reforming component from circulation water L1 that is a liquid. Therefore, gas phase G has a negative pressure than the gas phase formed by gas evaporated by Joule heat or the gas introduced from the outside. Since it is not necessary to evaporate circulation water L1 by applying a voltage, plasma P can be efficiently generated with a small voltage (that is, small power supply). Therefore, the reforming process of circulation water L1 can be rapidly and efficiently performed and the deodorizing process of the gas can be performed in a short period of time. That is, reforming liquid L2 containing air bubbles containing a radical (OH radical or the like), hydrogen peroxide, or the like is produced and gas 97 is bubbled in reforming liquid L2. Therefore, deodorization of gas 97 can be efficiently performed. In addition, since gas 97 can also be bubbled in storage tub 90, the deodorizing apparatus has a compact configuration as a whole. Furthermore, since water is not evaporated by Joule heat, the energy to be input is reduced. In addition, since gas for producing the reforming liquid is not introduced from the outside, the gas supply device for producing the reforming liquid is not necessary. The reforming liquid producing device 100 can be easily downsized, and deodorizing apparatus 101 can be easily downsized accordingly.

In addition, gas phase G that is formed by gas evaporated by Joule heat or gas introduced from the outside is difficult to be held in a certain shape or at a fixed position by buoyancy. However, in gas phase G of Embodiment 1, since a force is applied in a direction of gathering on center axis X1 by surrounding swirling flow F1, constant gas phase G can be produced in the vicinity of the right end portion 301 of first electrode 30. Therefore, an amount of gas produced between first electrode 30 and second electrode 31 varies little over time and electric power required for plasma P hardly changes. Therefore, plasma P can be stably generated and the reforming process of circulation water L1 can be efficiently and rapidly performed.

In addition, a volume of plasma P is less than or equal to a volume of the gas phase in the vicinity of the cathode electrode, but since a shape of gas phase G that is formed by gas evaporated by Joule heat or gas introduced from the outside is a bubble shape, the shape of gas phase G splits when the volume is greater than or equal to a certain volume. Therefore, it is difficult to generate plasma P greater than or equal to a certain volume. However, in gas phase G of Embodiment 1, if a swirling speed of swirling flow F1 can be secured, a volume in the direction of center axis X1 can be easily increased, so that the volume of plasma P can be easily increased. Therefore, the amount of the reforming component produced is easily increased and liquid can be rapidly reformed.

In addition, since the volume expands when the liquid evaporates, cavitation, which generates a shock wave and destroys a surrounding object, is known. In Embodiment 1, a position at which the destruction by the cavitation is most intensified is discharge portion 17 at which the inner diameter of processing tub 12 is the smallest and the swirling speed of swirling flow F1 is the fastest. Therefore, since right end portion 301 of first electrode 30 in gas phase G is far from a position at which the destruction of the cavitation is the strongest, the interference on first electrode 30 due to the cavitation becomes small and plasma P can be stability generated.

In addition, since the reforming process of circulation water L1 is performed without introducing air from the outside into reforming liquid producing device 100 when plasma P is generated, production of harmful nitrous acid can be suppressed. Nitrous acid is generated in plasma utilizing a gas phase introducing gas containing a nitrogen component of air or the like. Furthermore, reforming liquid L2 containing bubble BA, the OH radical, hydrogen peroxide, or the like can be produced.

Embodiment 2

Figure 6E:
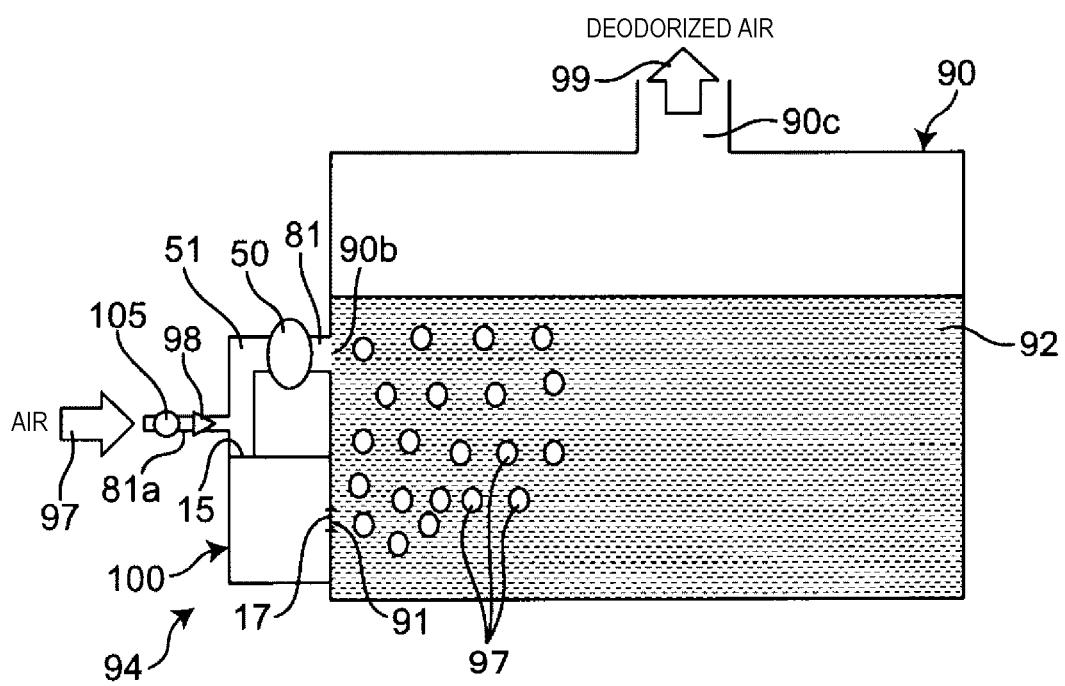
FIG. 6E is a sectional side view illustrating a configuration of a deodorizing apparatus according to Embodiment 2 of the disclosure.
Figure 6F:
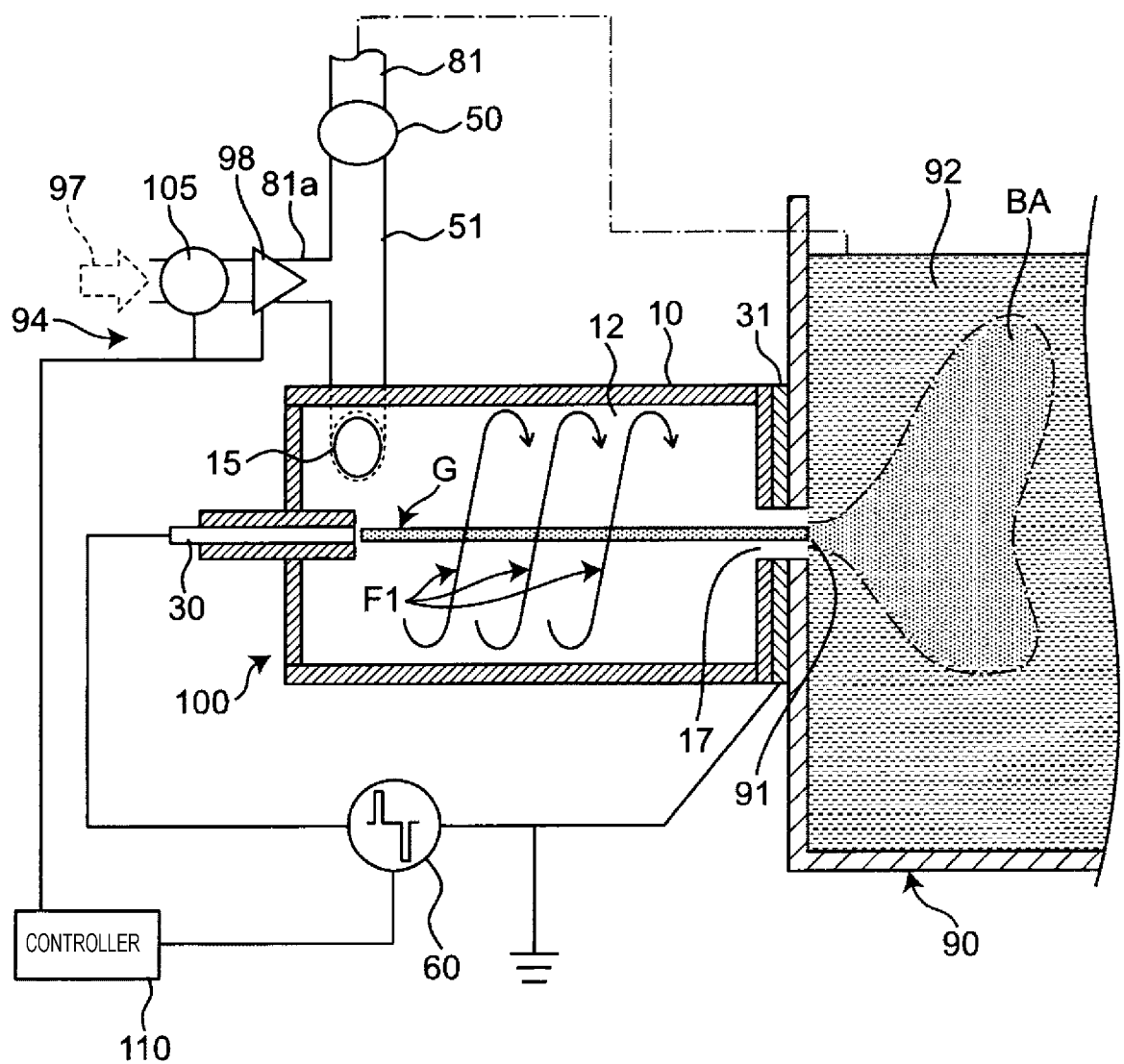
FIG. 6F is a partially enlarged sectional side view illustrating a detailed configuration of the deodorizing apparatus of FIG. 6E.

As illustrated in FIGS. 6E and 6F, branch pipe 81a is provided on a downstream side of liquid supplier 50 of circulation pipe 81, gas supply device 105 and opening and closing valve 98 are provided in branch pipe 81a, and thereby gas supplier 94 may be configured. The gas supply device 105 may be a pump. In gas supply device 105, gas 97 is taken in from the outside and gas 97 is sent into branch pipe 81a is an example of a pipe configuration of a gas passage. Opening and closing valve 98 opens and closes branch pipe 81a. Gas supply device 105, opening and closing valve 98, and power supply 60 can be driven and controlled by controller 110. In such a configuration, in a state where opening and closing valve 98 is closed, the reforming liquid producing process is completed. Then, for example, power supply 60 is turned off, and thereby generation of plasma P is stopped. Thereafter, gas 97 to be processed is supplied from branch pipe 81a to circulation water L1 in pipe 51 and is supplied into processing tub 12 via introduction portion 15 by driving gas supply device 105 and opening and closing valve 98.

Processing tub 12 is in a state where, for example, power supply 60 is turned off and the generation of plasma P is stopped. In this state, circulation water L1 from introduction portion 15 is introduced from a tangential direction of a circular cross-sectional shape orthogonal to center axis X1 of processing tub 12 to form swirling flow F1. A pressure in the vicinity of center axis X1 is lowered to less than or equal to the saturated water vapor pressure and water vapor in which a part of circulation water L1 is evaporated is generated by swirling flow F1. Thereby gas phase G is produced in the vicinity of center axis X1. In addition, gas phase G has a negative pressure by swirling flow F1. As a result, introduction of gas 97 into processing tub 12 is facilitated and gas 97 is mixed with gas phase G in processing tub 12. Furthermore, swirled gas phase G receives resistance of the storage water 92 in storage tub 90 in the vicinity of discharge portion 17 and thereby gas phase G is sheared by microbubbles or nano-bubbles. Gas phase G is diffused in storage water 92 of storage tub 90 via discharge portion 17 and reforming liquid supplier 91. That is, the odorous component of gas 97 is decomposed by the reforming component of reforming liquid L2. Gas is thereby deodorized by being bubbled in storage tub 90. Deodorized gas 99 advances upward in storage water 92 that is reforming liquid L2. Deodorized gas 99 is discharged from gas discharge portion 90c disposed at the upper portion of storage tub 90 to the outside of storage tub 90.

According to Embodiment 2, in addition to the same operational effects as those of Embodiment 1, circulation pipe 81 and processing tub 12 also serve as gas supplier 94 so that deodorizing apparatus 101 can be further easily downsized.

Embodiment 3

Figure 6G:
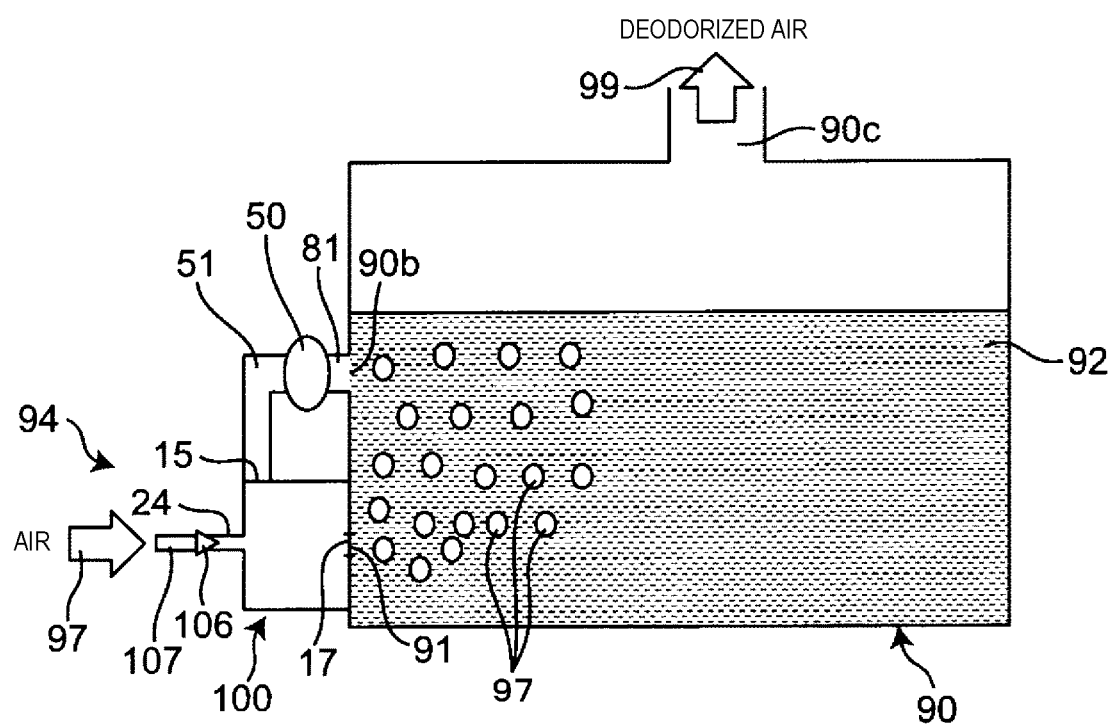
FIG. 6G is a sectional side view illustrating a configuration of a deodorizing apparatus according to Embodiment 3 of the disclosure.
Figure 6H:
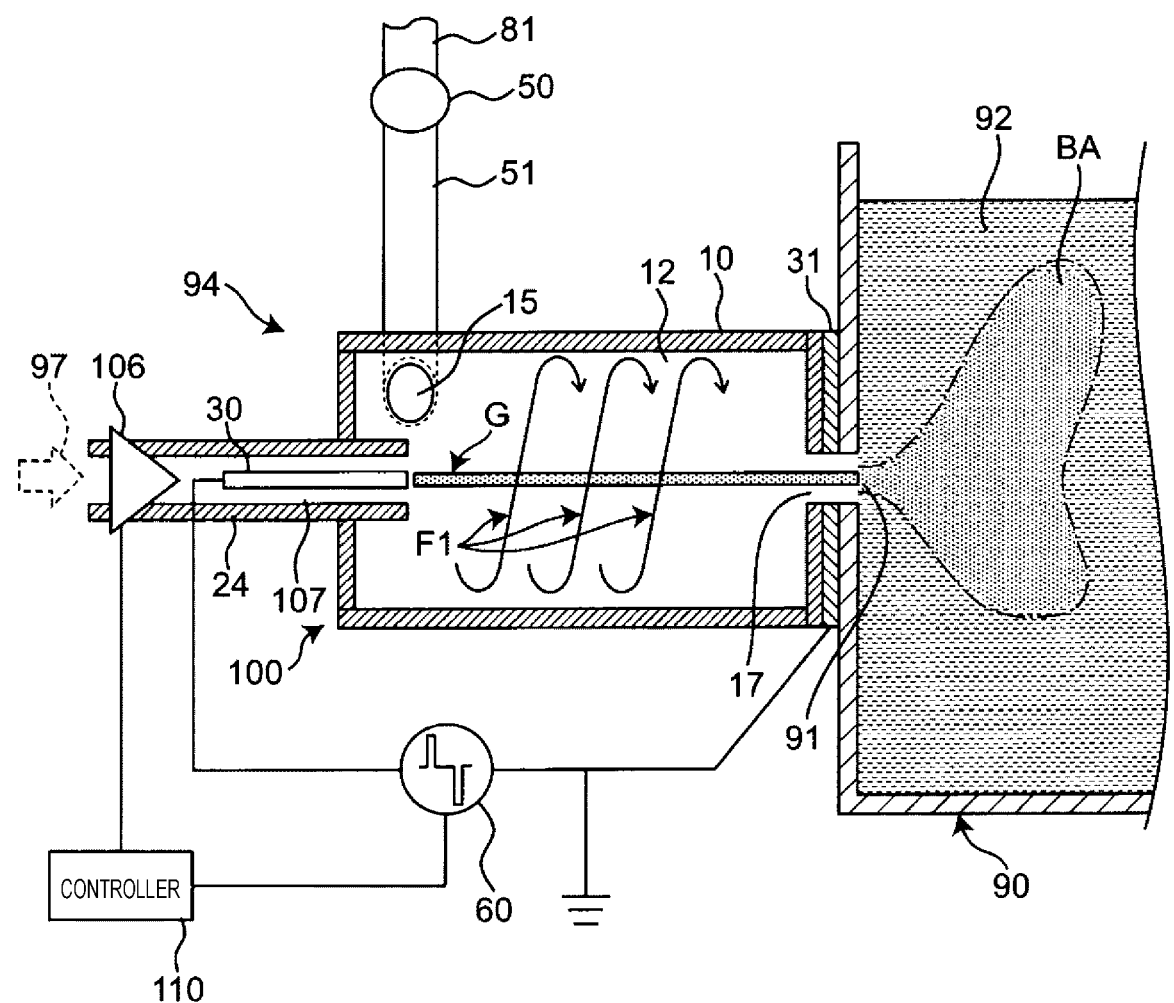
FIG. 6H is a partially enlarged sectional side view illustrating a detailed configuration of the deodorizing apparatus of FIG. 6G.

As illustrated in FIGS. 6G and 6H, first electrode 30 is supported by cylindrical electrode support tube 24 that is disposed at a center of second inner wall 22 of processing tub 12 and protrudes into accommodating space 83. Gas passage 107 is formed by providing a gap between electrode support tube 24 and first electrode 30. Opening and closing valve 106 is provided at an outside end portion of electrode support tube 24. Thereby gas supplier 94 may be configured in this manner. Opening and closing valve 106 opens and closes gas passage 107. Opening and closing valve 106 and power supply 60 can be driven and controlled by controller 110. In such a configuration, in a state where opening and closing valve 106 is closed, the reforming liquid producing process is completed. Then, for example, power supply 60 is turned off, and thereby the generation plasma P is stopped.

Thereafter, in processing tub 12, for example, in a state where power supply 60 is turned off and the generation is plasma P is stopped, circulation water L1 from introduction portion 15 is introduced from the tangential direction of the circular cross-sectional shape orthogonal to center axis X1 of processing tub 12, and thereby swirling flow F1 is formed. A pressure in the vicinity of center axis X1 is lowered to less than or equal to the saturated water vapor pressure. Water vapor in which a part of circulation water L1 is evaporated is generated by swirling flow F1, and thereby gas phase G is produced in the vicinity of center axis X1. In addition, gas phase G becomes a negative pressure by swirling flow F1. As a result, when opening and closing valve 106 is opened, gas 97 to be processed is sucked from gas passage 107 into processing tub 12 to be mixed with gas phase G. Furthermore, swirled gas phase G receives resistance of the storage water 92 in storage tub 90 in the vicinity of discharge portion 17 and thereby gas phase G is sheared by micro-bubbles or nano-bubbles. Gas phase G is diffused in storage water 92 of storage tub 90 via discharge portion 17 and reforming liquid supplier 91. That is, the odorous component of gas 97 is decomposed by the reforming component of reforming liquid L2. Gas 97 is thereby deodorized by being bubbled in storage tub 90. Deodorized gas 99 advances upward in storage water 92 that is reforming liquid L2 and is discharged from gas discharge portion 90c to the outside of storage tub 90. Gas discharge portion 90c is disposed at the upper portion of storage tub 90.

According to Embodiment 3, in addition to the same operational effects as those of Embodiment 1, gas passage 107 and processing tub 12 also serve as gas supplier 94 so that deodorizing apparatus 101 can be further easily downsized.

MODIFICATION EXAMPLES

The configuration of reforming liquid producing device 100 described in Embodiments 1 to 3 is an example and various changes can be provided. For example, the internal structure of processing tub 12, the position of first electrode 30 or second electrode 31, or the like is not limited to the structure of Embodiments 1 to 3.

Figure 7:
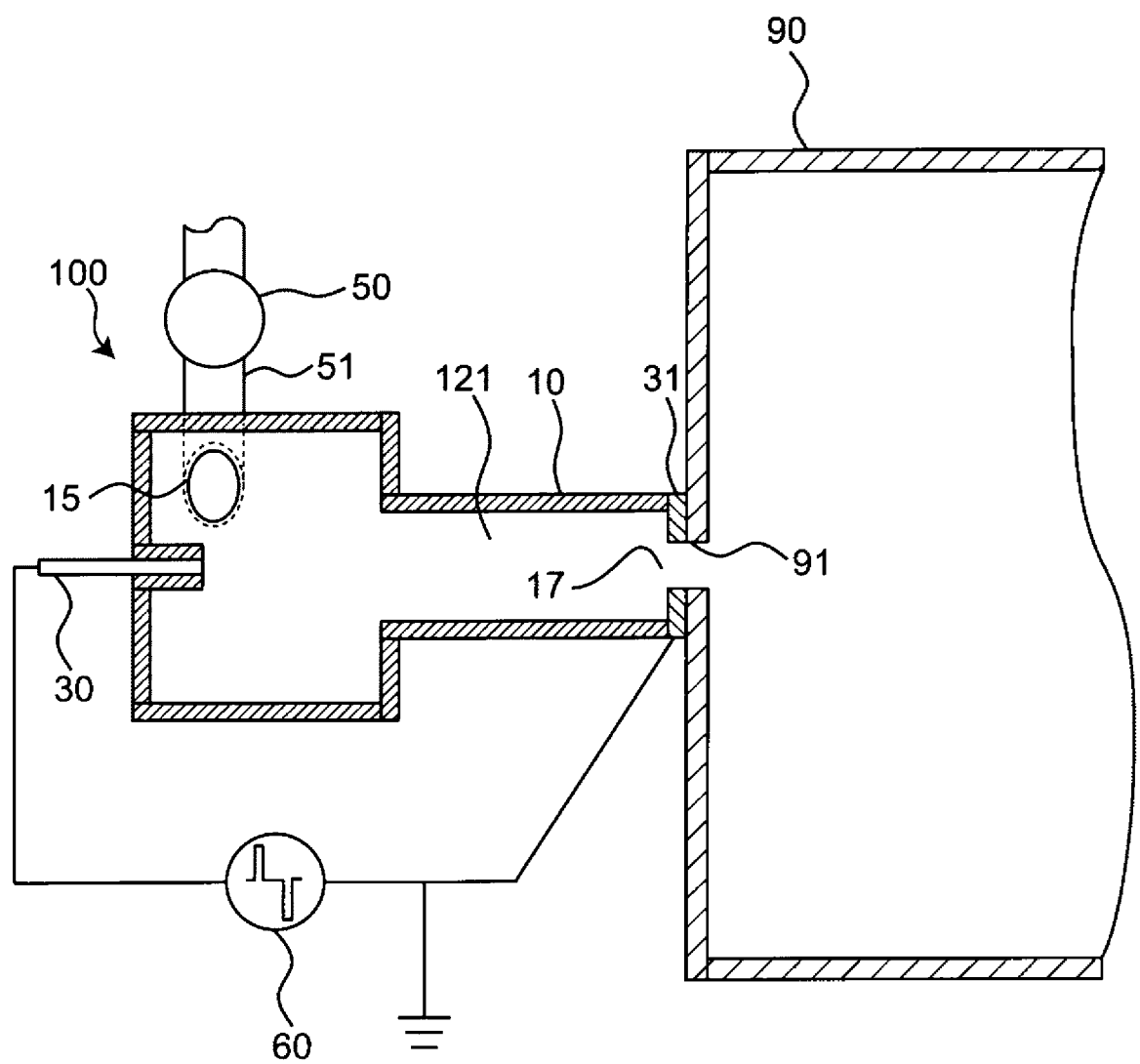
FIG. 7 is a side sectional view illustrating a modification example of a device body.
Figure 8:
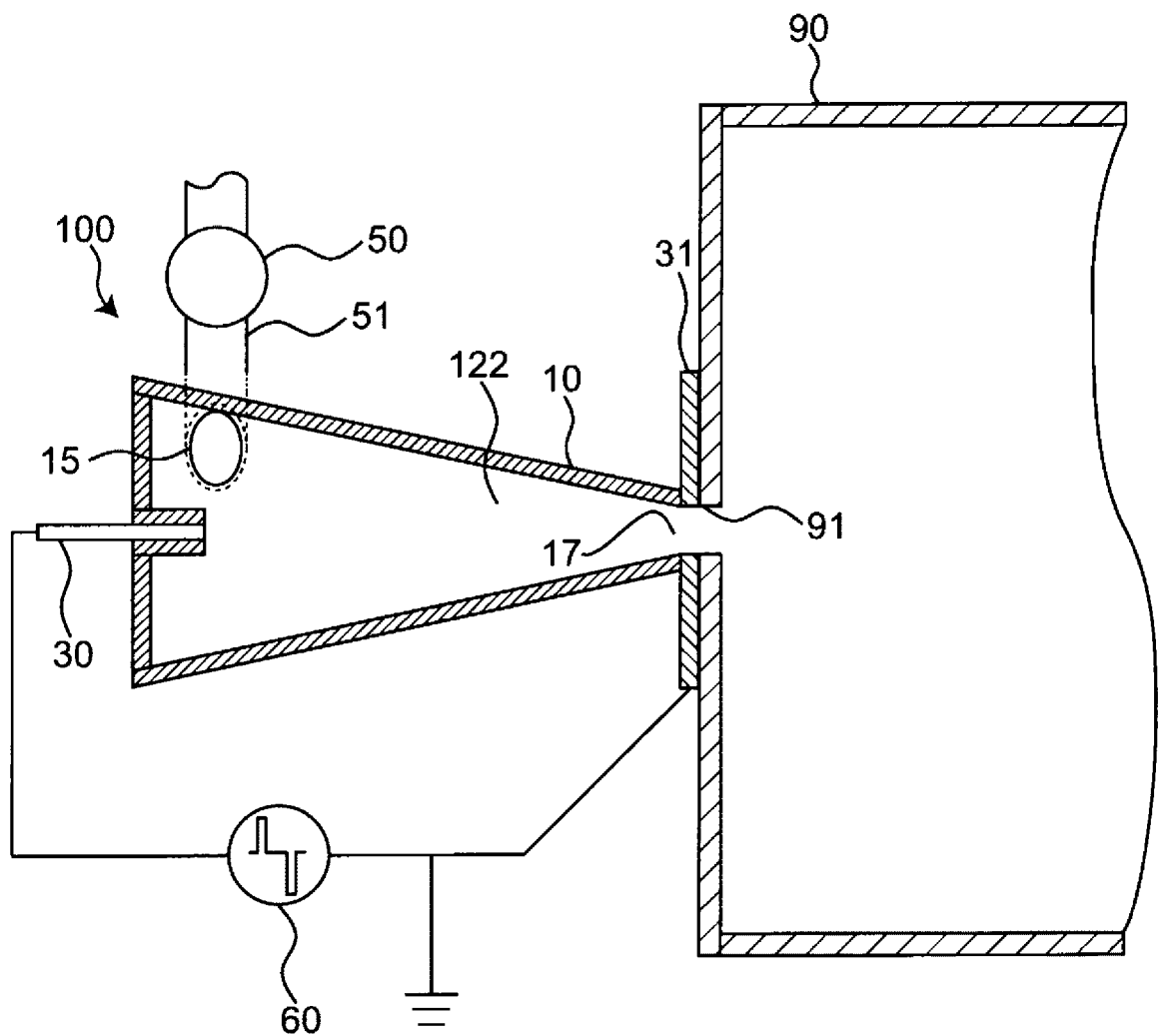
FIG. 8 is a side sectional view illustrating a modification example of a device body.

In Embodiments 1 to 3, processing tub 12 has a simple cylindrical shape, but as long as it is a cylindrical processing tub having a circular cross-sectional shape and a narrowed and hole-shaped discharge portion is provided on the center axis or in the vicinity of the center axis of the processing tub at one end portion of the processing tub, various shapes can be provided. For example, as illustrated in FIG. 7, the same effect can be obtained even in processing tub 121 combining cylinders having different radii. In FIG. 7, a radius on the introduction portion side is larger than a radius on the discharge portion side. Alternatively, the same effect can be obtained even in conical shaped processing tub 122 illustrated in FIG. 8. Preferably, in order to prevent swirling flow F1 from sliding in the forward direction F, as illustrated in FIG. 8, the conical shape of which an inner diameter of a cross-section continuously decreases is preferable.

Figure 9A:
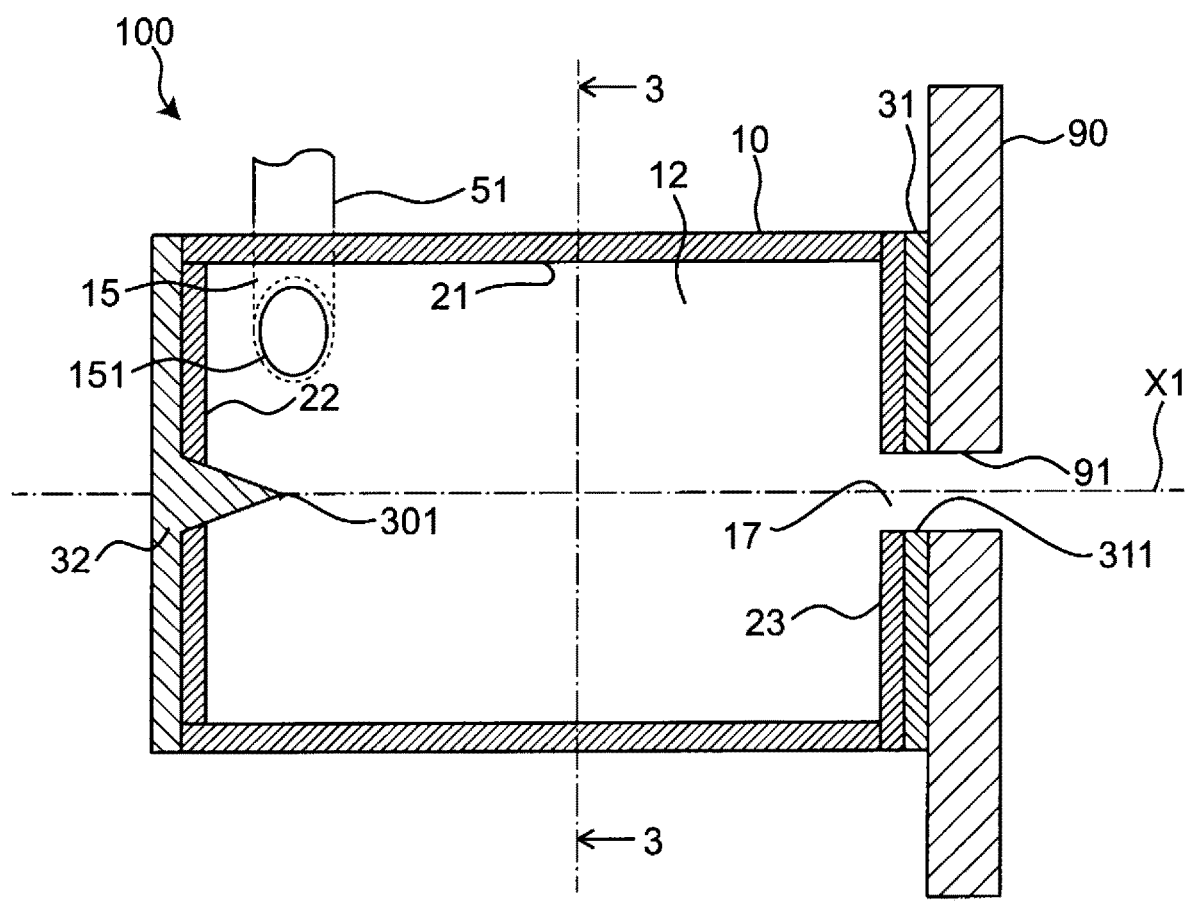
FIG. 9A is a side sectional view illustrating a modification example of a device body.
Figure 9A:
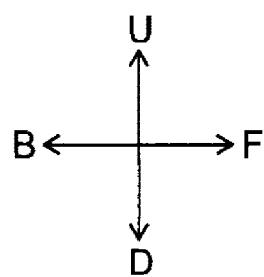
Figure 9B:
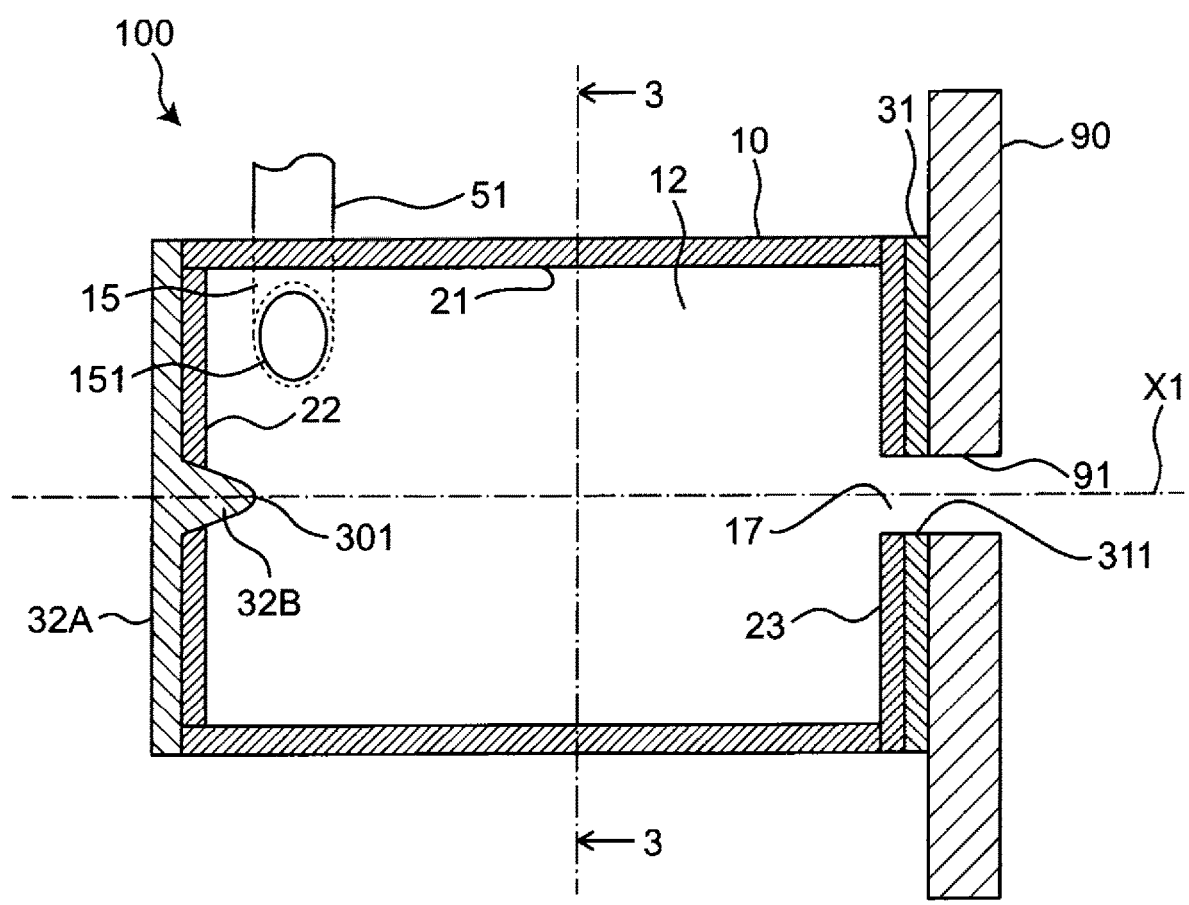
FIG. 9B is a side sectional view illustrating a modification example of a device body different from that of FIG. 9A.
Figure 9B:
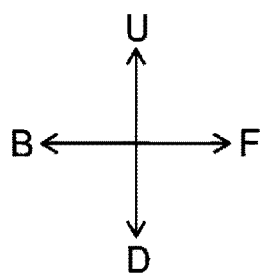

In addition, in Embodiments 1 to 3, the shape of first electrode 30 is a rod shape, but it is not limited to the embodiments as long as first electrode 30 has a shape in which electrolysis is concentrated on right end portion 301 of first electrode 30. For example, as illustrated in FIG. 9A, plate-like first electrode 32 having a conical shape pointed toward the discharge portion side may be provided. In addition, as illustrated in FIG. 9B, instead of the conical shape, plate-like first electrode 32A having mountain-shaped protrusion 32B protruding so as to curve toward the discharge portion side may be provided. In first electrode 32A, a center portion closest to generated plasma P tends to wear out, so that it is preferable that the electrode having mountain-shaped protrusion 32B of which the center portion protrudes inward the processing tub 12 has a longer life than that of a simple flat electrode. More preferably, instead of plate-like first electrode 32, when the electrode is worn, a rod electrode, which facilitates delivery of an electrode inside processing tub 12, may be provided.

Figure 10:
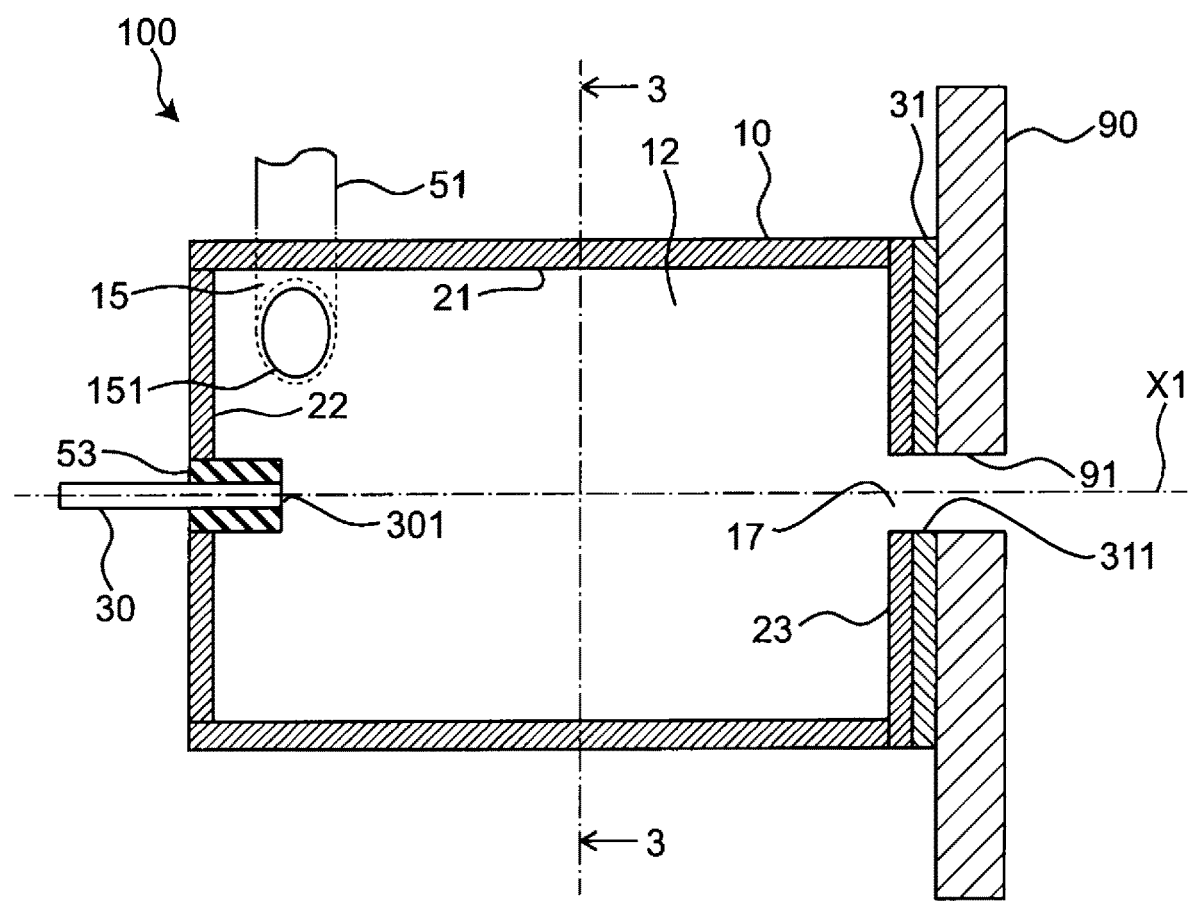
FIG. 10 is a side sectional view illustrating a modification example of a device body.
Figure 10:
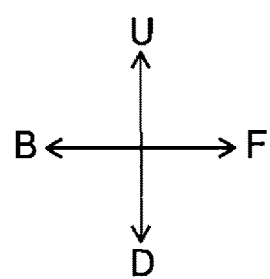

In addition, as illustrated in FIG. 10, the same effect can be obtained by adopting a structure in which first electrode 30 and insulator 53 are attached to second inner wall 22 without using electrode support tube 24 of first electrode 30. Preferably, in order to suppress the electrolysis of water or the generation of Joule heat, an insulator may be covered except for a connecting portion between right end portion 301 of first electrode 30 which is necessary for generating plasma and power supply 60.

In addition, in Embodiments 1 to 3, the material of first electrode 30 is tungsten as an example, but it is not limited to the embodiments as long as it is a material particularly having conductivity. Preferably, a metal material capable of exhibiting a high sterilization effect by causing a Fenton reaction when the metal material is in contact with hydrogen peroxide in water may be provided. An electrode having a copper or iron-containing component, for example, an electrode made of stainless steel (SUS), copper, or copper tungsten may be used. A metal material capable of exhibiting a high sterilization effect by causing such a Fenton reaction can be used as a material of a pipe such as circulation pipe 81.

Furthermore, if the electrode containing copper or iron component necessary for the Fenton reaction is used for first electrode 30, the electrode material becomes nano-particles, the Fenton reaction is accelerated, and deodorization is accelerated.

Figure 11:
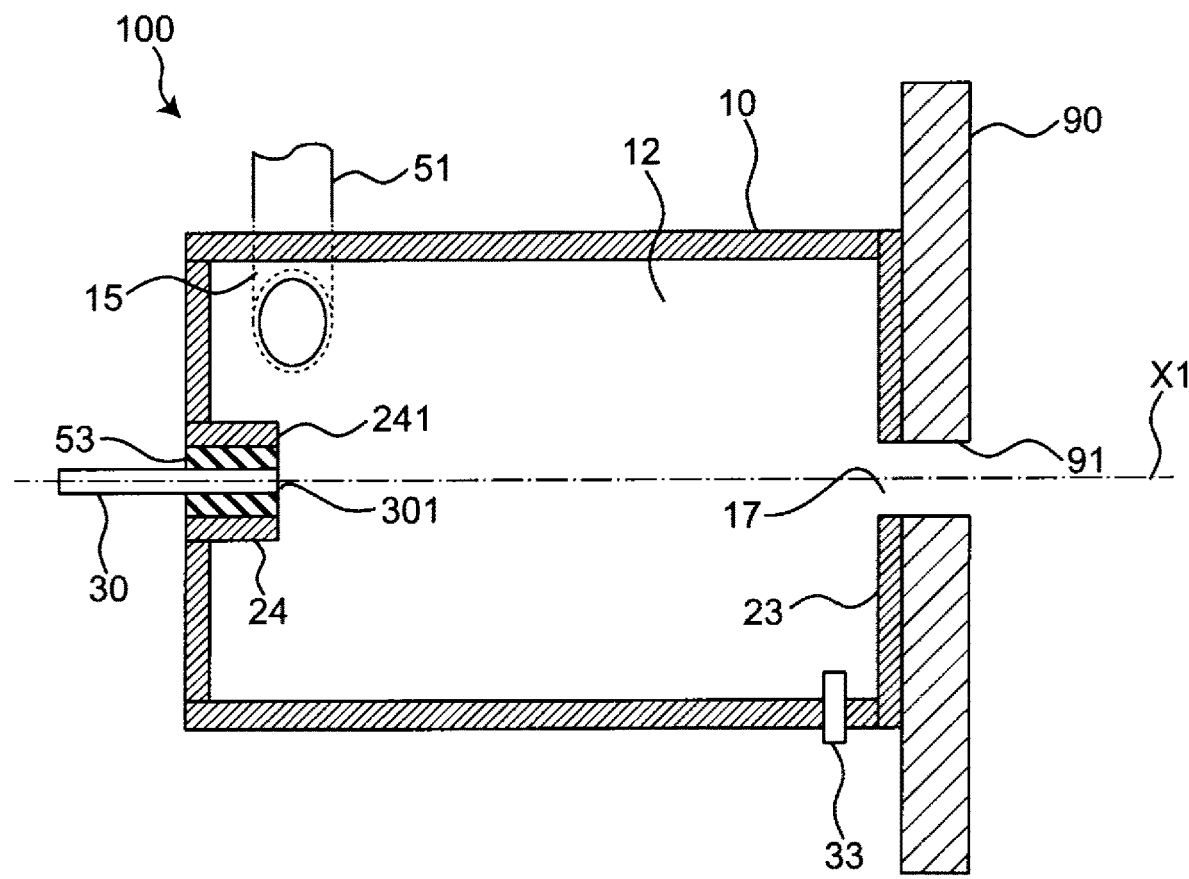
FIG. 11 is a side sectional view illustrating a modification example of a device body.
Figure 11:
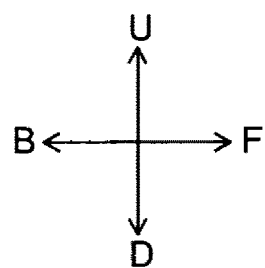
Figure 12:
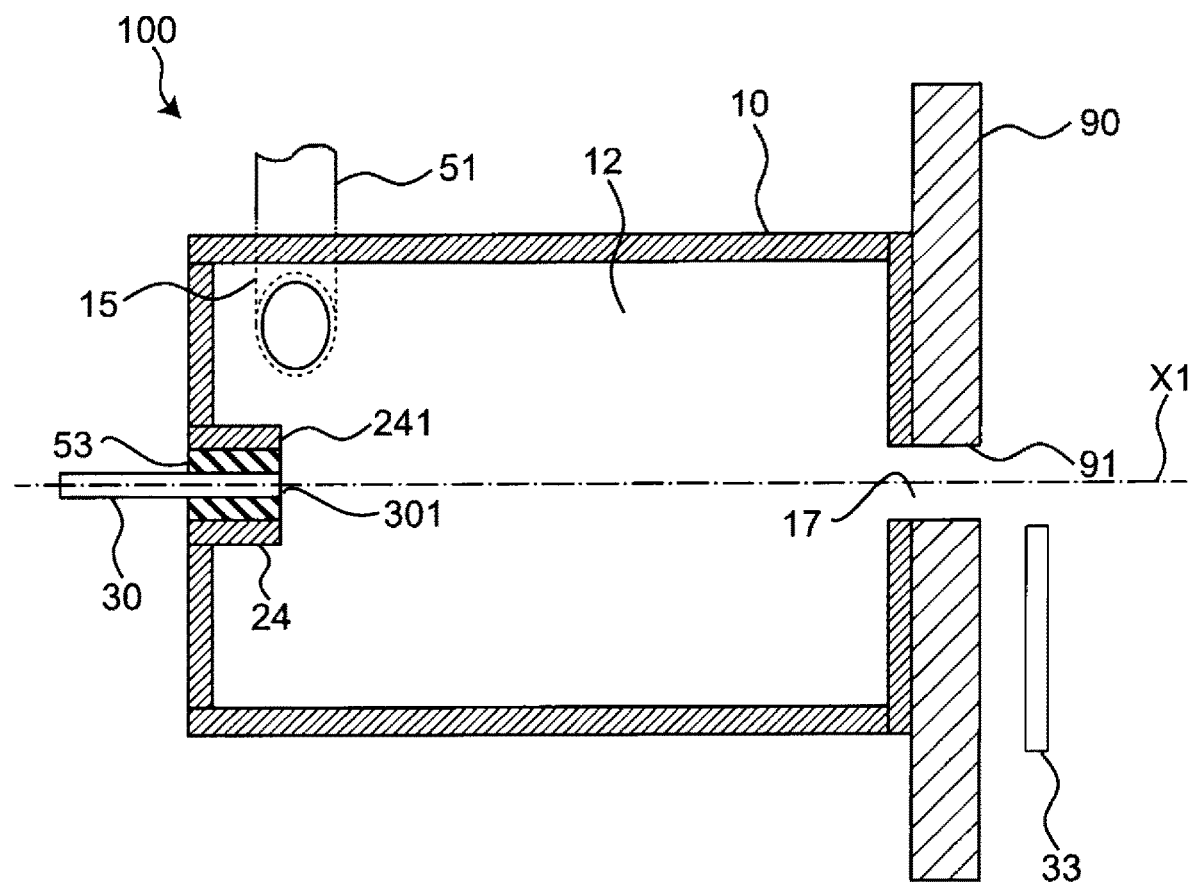
FIG. 12 is a side sectional view illustrating a modification example of a device body.
Figure 12:
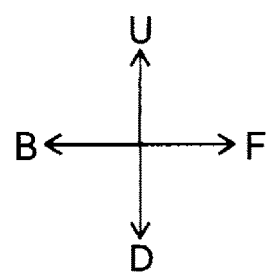
Figure 13:
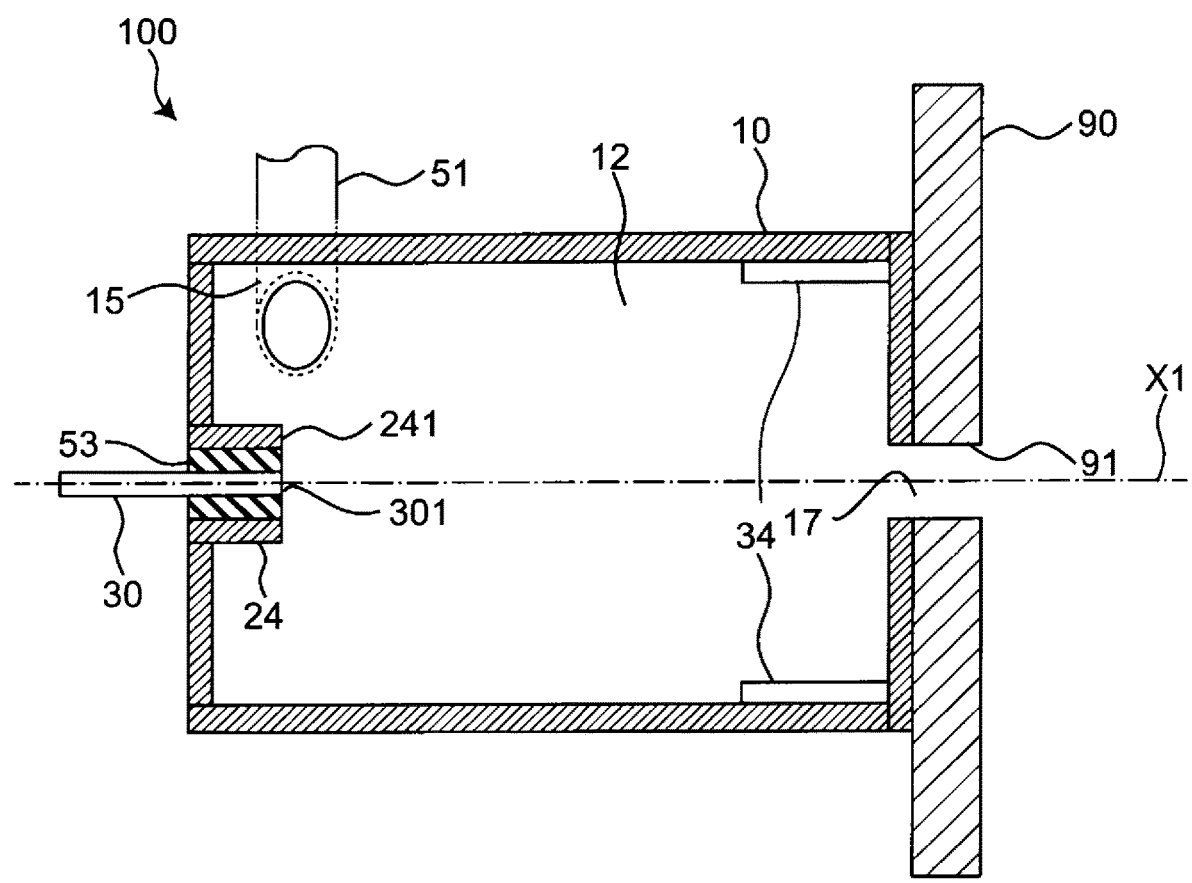
FIG. 13 is a side sectional view illustrating a modification example of a device body.
Figure 13:
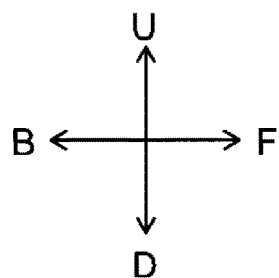

In Embodiments 1 to 3, second electrode 31 is disposed at discharge portion 17, but it is not limited to the embodiments as long as at least a part of the grounded second electrode is disposed inside processing tub 12. For example, as for the disposition location, as illustrated in FIG. 11, the same effect can be obtained even if rod-like second electrode 33 is disposed on one side of first inner wall 21 in center axis X1. In addition, as illustrated in FIG. 12, rod-like second electrode 33 may be disposed outside processing tub 12, inside storage tub 90, and in the vicinity of reforming liquid supplier 91 of storage tub 90. In addition, as illustrated in FIG. 13, cylindrical second electrode 34 may be disposed inside first inner wall 21. In addition, opening 311 has a cylindrical shape, but it may be a polygonal shape, or the second electrode may be formed by combining a plurality of divided metal members. Preferably, in order not to disturb swirling flow F1, a plate shape or a cylindrical shape having a round hole may be provided. In addition, the shorter the distance between gas phase G and the second electrode is, the smaller the resistance of water is, so that the Joule heat can be suppressed. Therefore, it is preferable that the second electrode is disposed at discharge portion 17 or in the vicinity of discharge portion 17 at which the distance between gas phase G and the second electrode is short.

A flow rate of circulation water L1 introduced into processing tub 12 is set to a flow rate at which gas phase G is generated in swirling flow F1 according to the shape of processing tub 12. In addition, the pulse voltage applied to first electrode 30 and second electrode 31 may be monopolar instead of bipolar, or a voltage, a pulse width, a frequency, or the like may be appropriately set to a value at which plasma P can be generated in gas phase G generated in swirling flow F1.

Furthermore, power supply 60 may be a high-frequency power supply or the like other than a pulse power supply as long as the effect of the disclosure can be obtained. Preferably, since the pH between electrodes is biased due to the electrolysis of water, bipolar application may be provided so that the cathode and the anode can be alternately exchanged.

Figure 14A:
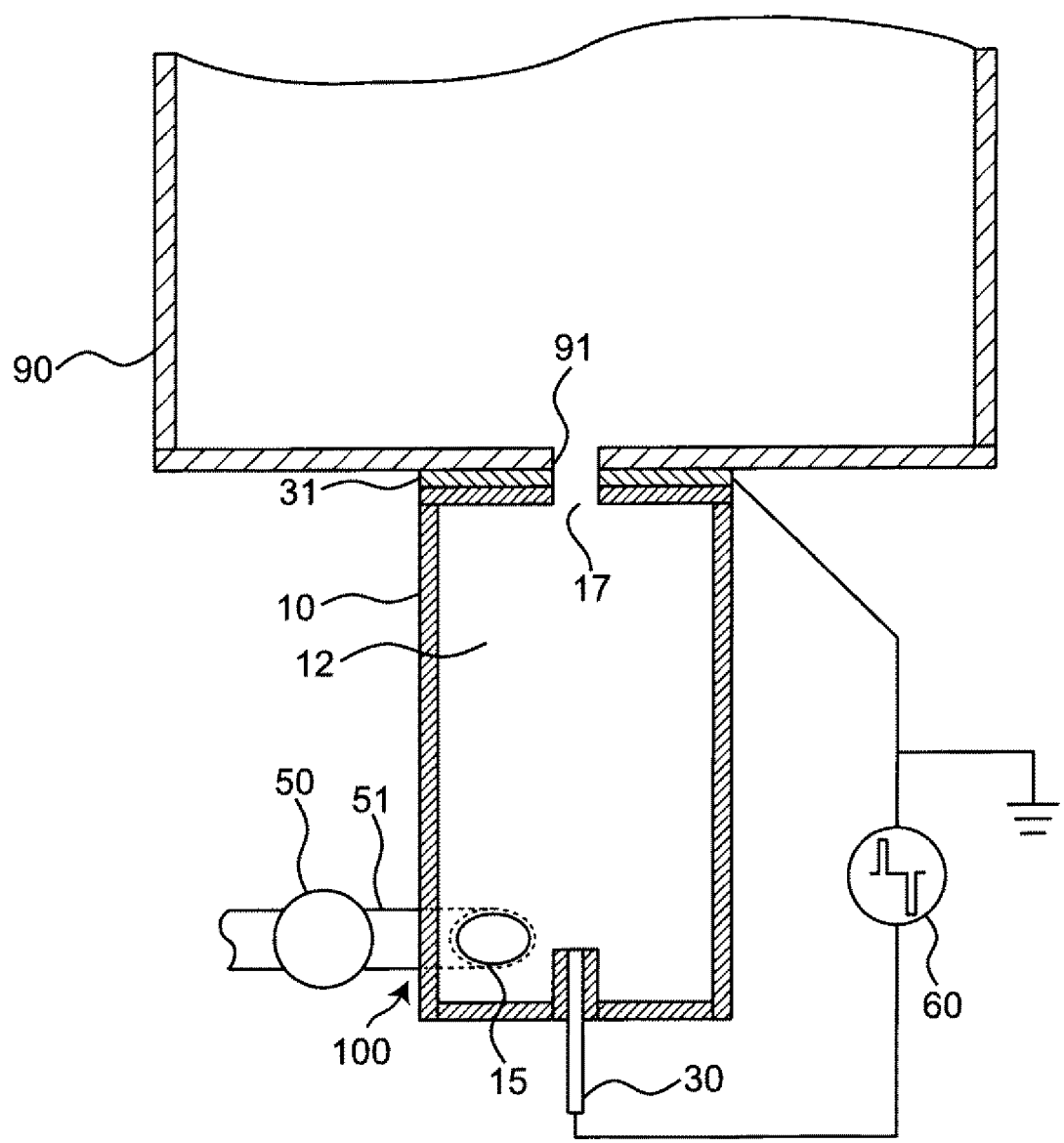
FIG. 14A is a side sectional view illustrating a modification example of a device body.
Figure 14A:
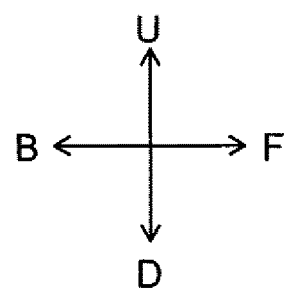

Storage tub 90 is a tub, but it is not limited to the tub as long as the shape in which the water can be held in storage tub 90 is provided in order to shear swirling flow F1. For example, it may be a pipe for transporting the reforming liquid. Preferably, in order to fill discharge portion 17 with circulation water L1 and prevent air from entering processing tub 12, as illustrated in FIG. 14A, device body 10 discharges the reforming liquid upward and storage tub 90 may be on the upper side of device body 10.

Figure 14B:
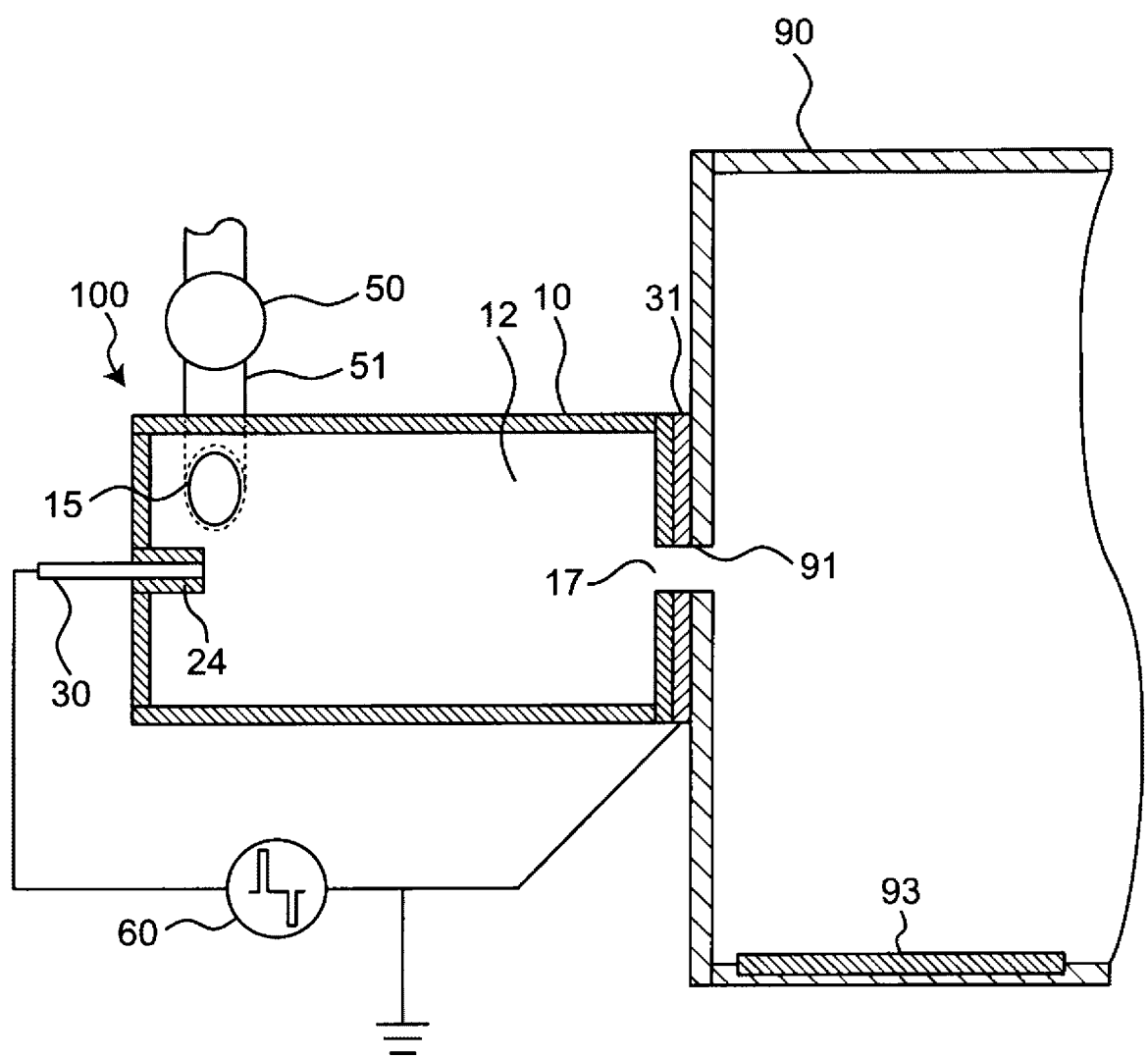
FIG. 14B is a side sectional view illustrating that a copper material is disposed in a part of a storage tub in the modification example of a device body.
Figure 15:
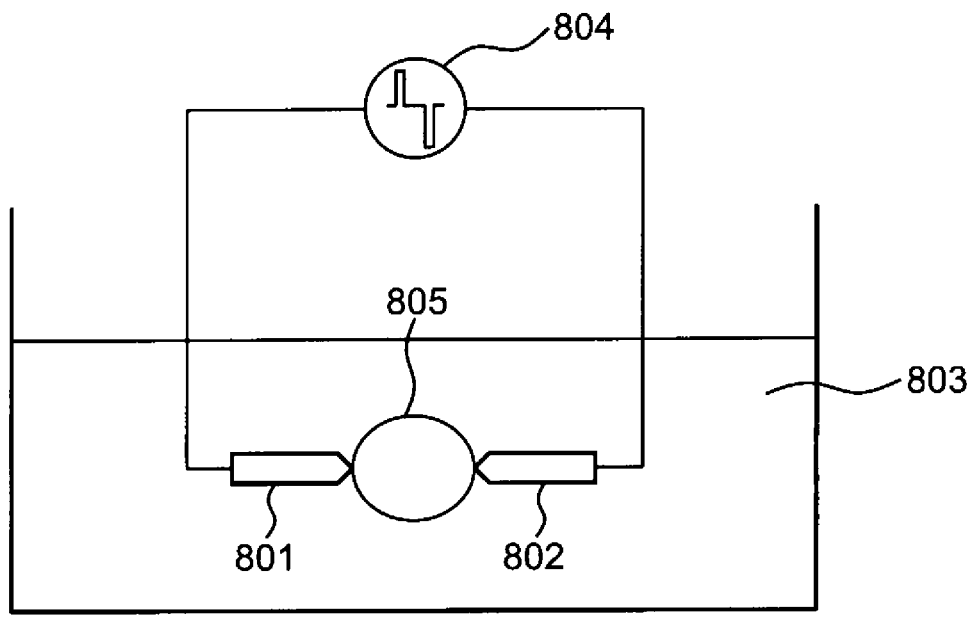
FIG. 15 is a schematic configuration view of a reforming liquid producing device of the related art.
Figure 16:
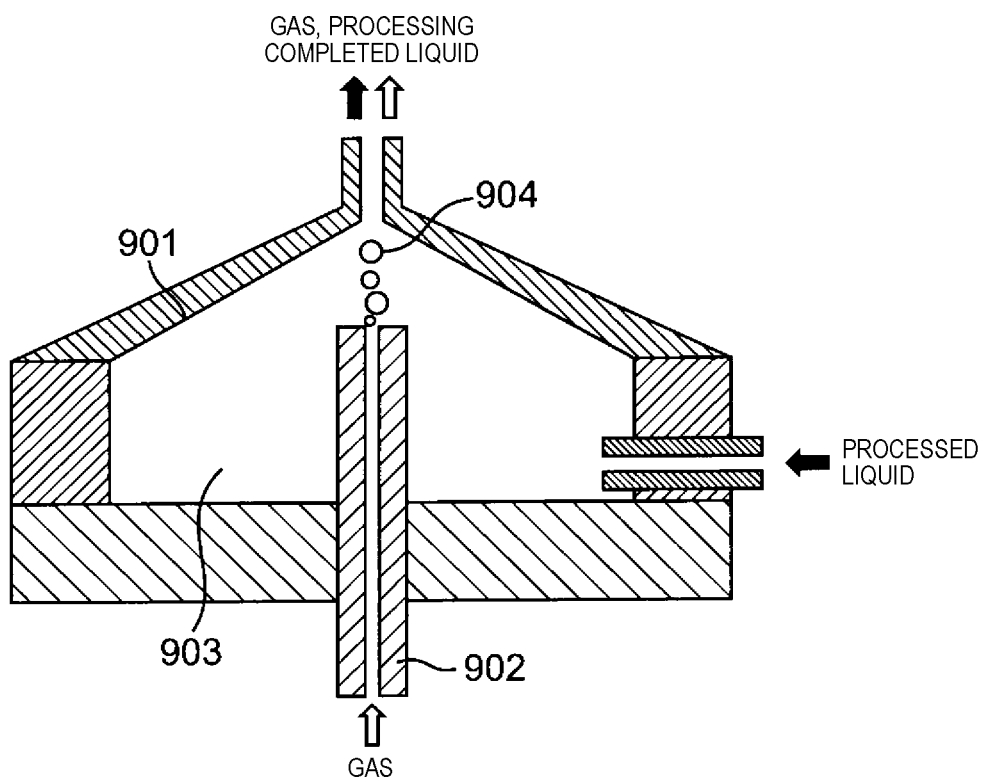
FIG. 16 is a schematic configuration view of the reforming liquid producing device of the related art including a gas introducing device.

In addition, as a material configuring storage tub 90, it is sufficient that water does not permeate. In addition, for example, as illustrated in FIG. 14B, plate member 93 containing copper or iron capable of exhibiting a high sterilization effect by causing the Fenton reaction with hydrogen peroxide water which is one of the reforming components can be used for a part of or all storage tub 90. In addition, plate member 93 may be disposed in storage tub 90 as a member separated from storage tub 90. In short, when plate member 93 comes into contact with the reforming liquid in storage tub 90, a high sterilization effect by causing the Fenton reaction with hydrogen peroxide water which is one of the reforming components can be exhibited.

In Embodiments 1 to 3, circulation water L1 is reformed, but the liquid to be reformed may not be limited to water. For example, it may be ethanol.

Although Embodiments 1 to 3 of the disclosure are described above, Embodiments 1 to 3 described above are merely examples for implementing the disclosure. Therefore, the disclosure is not limited to Embodiments 1 to 3, and Embodiments 1 to 3 described above can be appropriately modified and implemented without departing from the spirit of the disclosure.

That is, it is possible to achieve each of the effects provided therein by appropriately combining an arbitrary embodiment, a modification example of the embodiment, or the various modification examples described above. In addition, a combination of the embodiments, a combination of the examples, or a combination of the embodiments and the examples is possible and a combination of features in different embodiments or examples is also possible.

The deodorizing apparatus and the deodorizing method according to the aspects of the disclosure can produce the reforming liquid containing the reforming component (liquid-derived radical, compound, or the like) from the liquid by generating plasma in the liquid and deodorize gas from the produced reforming liquid. Therefore, the deodorizing apparatus and the deodorizing method according to the aspects of the disclosure can be utilized for environmental improvement such as gas deodorization and the like. The deodorizing apparatus can also be used as a gas purifier with a humidifying function in a household or an office.

What is claimed is:

1. A deodorizing apparatus comprising:
   a processing tub that includes an introduction portion, into which liquid is introduced, and a discharge portion, and that is configured to swirl the liquid between the introduction portion and the discharge portion around a center axis to generate a swirling flow and generate a gas phase in a vicinity of a swirling center of the swirling flow, and that discharges the liquid from the discharge portion as a reforming liquid after swirling the liquid;
   a first electrode of which at least a part is disposed in the processing tub and comes into contact with the liquid in the processing tub;
   a second electrode that is disposed so as to come into contact with the liquid in the processing tub;
   a power supply that generates plasma in the gas phase by applying a voltage between the first electrode and the second electrode to produce a reforming component in the reforming liquid;
   a storage tub that includes a reforming liquid supplier to which the discharge portion of the processing tub is connected and the reforming liquid is supplied, and a gas discharge portion which discharges gas after deodorization to an upper portion above the reforming liquid supplier, and in which the produced reforming component is dissolved in the liquid and is dispersed in the liquid to produce the reforming liquid, wherein the produced reforming liquid is discharged from the processing tub and is stored in the storage tub; and
   a gas supplier that supplies gas into the reforming liquid in the storage tub,
   wherein the gas is supplied from the gas supplier into the storage tub, and the supplied gas has a bubble shape and comes into contact with the reforming liquid stored in the storage tub.

2. The deodorizing apparatus of claim 1,
   wherein the gas supplier includes a gas blowout unit that is disposed below the gas discharge portion and the reforming liquid supplier of the storage tub and blows out the gas so as to be supplied into the reforming liquid in the storage tub.

3. The deodorizing apparatus of claim 1,
   wherein the gas supplier includes a gas supply device that is disposed in a branch pipe connected to a circulation pipe through which the liquid in the storage tub is supplied from the storage tub to the introduction portion of the processing tub to supply the gas to the branch pipe, and
   an opening and closing valve that opens and closes between the branch pipe and the circulation pipe.

4. The deodorizing apparatus of claim 1,
wherein the gas supplier includes a gas passage through which the gas is supplied along the center axis from a vicinity of the first electrode of the processing tub, and
an opening and closing valve that opens and closes the gas passage.

5. The deodorizing apparatus of claim 1,
wherein as the first electrode, an electrode having a copper or iron-containing component is used.

6. The deodorizing apparatus of claim 1,
wherein the first electrode is disposed so as to come into contact with the gas phase generated in the vicinity of the swirling center of the swirling flow of the liquid or be positioned in a vicinity of the gas phase.

7. The deodorizing apparatus of claim 1,
wherein the processing tub includes a cylindrical or truncated conical first inner wall that generates the swirling flow by swirling the liquid supplied from the introduction portion, and
wherein the first electrode is disposed on a center axis or in a vicinity of the center axis of the first inner wall.

8. The deodorizing apparatus of claim 7,
wherein the first electrode is disposed on one end portion side of the center axis or the vicinity of the center axis,
wherein the second electrode is disposed on an other end portion side of the center axis or the vicinity of the center axis,
wherein the introduction portion is disposed on the one end portion side of the center axis, and
wherein the discharge portion is disposed on the other end portion side of the center axis.

9. The deodorizing apparatus of claim 8,
wherein the second electrode is a plate-like electrode that is disposed so as to surround a part around the center axis of the first inner wall on an other end portion side of the first inner wall or an entire circumference of the center axis.

10. The deodorizing apparatus of claim 8,
wherein the second electrode is disposed on a side of the center axis of the first inner wall on an other end portion side of the first inner wall.

11. The deodorizing apparatus of claim 8,
wherein the second electrode is a cylindrical electrode that is disposed so as to surround a part of the center axis of the first inner wall on an other end portion side of the first inner wall or an entire circumference of the center axis.

12. The deodorizing apparatus of claim 1,
wherein the storage tub includes a plate member configured to cause a Fenton reaction with an OH radical or hydrogen peroxide in the reforming liquid.

13. The deodorizing apparatus of claim 12,
wherein the plate member contains copper or iron.

14. The deodorizing apparatus of claim 12,
wherein the plate member forms part or all of the storage tub.

15. The deodorizing apparatus of claim 12,
wherein the plate member is disposed inside the storage tub as a member separated from the storage tub.

* * * * *